United States Patent
Just et al.

(10) Patent No.: US 6,740,108 B1
(45) Date of Patent: May 25, 2004

(54) THERMAL TREATMENT CATHETER HAVING PREFERENTIAL ASYMMETRICAL HEATING PATTERN

(75) Inventors: Dale Just, Minneapolis, MN (US); Eric N. Rudie, Maple Grove, MN (US); Jonathan L. Flachman, Robbinsdale, MN (US); Scott Stockmoe, Flagstaff, AZ (US); Aaron Hjelle, Champlin, MN (US); Bruce W. Ebner, Shorewood, MN (US); Joel Crabb, Minneapolis, MN (US); Stanley E. Kluge, Watertown, MN (US)

(73) Assignee: Urologix, Inc., Minneapolis, MN (US)

( * ) Notice: Subject to any disclaimer, the term of this patent is extended or adjusted under 35 U.S.C. 154(b) by 77 days.

(21) Appl. No.: 10/115,158

(22) Filed: Apr. 3, 2002

Related U.S. Application Data

(60) Provisional application No. 60/281,891, filed on Apr. 5, 2001.

(51) Int. Cl.[7] ............................................. A61F 7/00

(52) U.S. Cl. ............................... 607/96; 607/101

(58) Field of Search ...................... 606/27–29, 13–16; 607/96, 98, 99, 101–102

(56) References Cited

U.S. PATENT DOCUMENTS

| | | |
|---|---|---|
| 3,228,400 A | 1/1966 | Armao |
| 4,204,549 A | 5/1980 | Paglione |
| 4,311,154 A | 1/1982 | Sterzer et al. |
| 4,573,966 A | 3/1986 | Weiki et al. |
| 4,583,556 A | 4/1986 | Hines et al. |
| 4,601,296 A | 7/1986 | Yerushalmi |

(List continued on next page.)

FOREIGN PATENT DOCUMENTS

| | | |
|---|---|---|
| CH | 1 238 200 | 7/1971 |
| DE | 30 11 322 | 9/1980 |
| DE | 3707921 A1 | 3/1987 |
| DE | 3730494 A1 | 3/1988 |
| EP | 0 246 176 | 5/1987 |
| EP | 0 370 890 | 11/1989 |
| EP | 0 459 535 A2 | 11/1989 |
| EP | 0 597 463 A2 | 11/1993 |
| EP | 0 643 982 A1 | 6/1994 |
| EP | 0 648 515 A1 | 10/1994 |
| JP | 4-28377 | 1/1992 |
| WO | WO 89/02292 | 3/1989 |
| WO | WO 93/01752 | 2/1993 |
| WO | WO 93/20767 | 10/1993 |
| WO | WO 93/25136 | 12/1993 |
| WO | WO 94/26188 | 11/1994 |
| WO | WO 95/17132 | 6/1995 |

OTHER PUBLICATIONS

"Cooled microwave transrectal applicator with adjustable directional beam for prostate treatment" by P.S. Debick et al., *International Journal of Hyperthermia*, vol. 11, No. 1, Jan.–Feb. 1995.

(List continued on next page.)

Primary Examiner—Roy D. Gibson
(74) Attorney, Agent, or Firm—Kinney & Lange, P.A.

(57) ABSTRACT

A thermal therapy catheter for preferentially treating tissue adjacent to a body lumen includes a catheter shaft that is insertable into the body lumen. An energy-emitting element is carried by the catheter shaft, and is operable to radiate a generally symmetrical energy pattern. The catheter shaft includes a plurality of cooling lumens around the energy-emitting element, configured for circulation of a fluid therethrough. An attenuating element is located in at least one of the plurality of cooling lumens and is arranged to modify the generally symmetrical energy pattern radiated by the energy-emitting element to deliver an asymmetrical energy pattern to the tissue adjacent to the body lumen.

22 Claims, 17 Drawing Sheets

U.S. PATENT DOCUMENTS

| | | | |
|---|---|---|---|
| 4,612,940 A | | 9/1986 | Kasevich et al. |
| 4,700,716 A | | 10/1987 | Kasevich et al. |
| 4,776,086 A | | 10/1988 | Kasevich et al. |
| 4,825,880 A | | 5/1989 | Stauffer et al. |
| 4,832,023 A | | 5/1989 | Murphy-Chutorian et al. |
| 4,841,988 A | | 6/1989 | Fetter et al. |
| 4,872,458 A | | 10/1989 | Kanehira et al. |
| 4,913,142 A | | 4/1990 | Kittrell et al. |
| 5,061,267 A | | 10/1991 | Zeiher |
| 5,097,845 A | | 3/1992 | Fetter et al. |
| 5,151,100 A | | 9/1992 | Abele et al. |
| 5,213,097 A | | 5/1993 | Zeindler |
| 5,301,687 A | | 4/1994 | Wong et al. |
| 5,330,518 A | | 7/1994 | Neilson et al. |
| 5,364,392 A | | 11/1994 | Warner et al. |
| 5,383,917 A | | 1/1995 | Desai et al. |
| 5,391,197 A | | 2/1995 | Burdette et al. |
| 5,405,346 A | | 4/1995 | Grundy et al. |
| 5,413,588 A | | 5/1995 | Rudie et al. |
| 5,484,433 A | | 1/1996 | Taylor et al. |
| 5,496,271 A | * | 3/1996 | Burton et al. .............. 607/27 |
| 5,498,227 A | | 3/1996 | Mawad |
| 6,427,089 B1 | * | 7/2002 | Knowlton .............. 607/101 |
| 6,675,050 B2 | * | 1/2004 | Arndt et al. ............. 607/101 |

OTHER PUBLICATIONS

"Transurethral Microwave Thermotherapy (TUMT)" by Devonec, Tomera, & Perrin, *Monographs in Urology*, vol. 13, No. 4, 1992.

"Heating characteristics of a helical microwave applicator for transurethral hyperthermia of benign prostatic hyperplasia" by Astrahan et al., *Int. J. Hyperthermia*, vol. 7, No. 1, 1991.

"Design of intracavitary microwave applicators for the treatment of uterine cervix carcinoma" by D. J. Li et al, *Int. J. Hyperthermia*, vol. 7, No. 5, 1991.

"Heat production in microwave–irradiated thermocouples" by Dunscombe & McLellan, *Am. Assoc. Phys. Med.*, Jul./Aug. 1986.

"Interstitial Equal–Phased Arrays for EM Hyperthermia" by Turner, *IEEE Transactions on Microwave Theory and Techniques*, Vo. MTT–34, No. 5, May 1986.

"Design and Thermometry of an Intracavitary Microwave Applicator Suitable for Treatment of Some Vaginal and Rectal Cancers" by Ding–Jiu et al, *Int. J. Radiation Oncology Biol. Phys, Technical Innovations and Notes*, vol. 10, 1984.

"Microstrip Loop Radiators for Medical Applications" by Bahl et al, *IEEE Transactions on Microwave Theory and Techniques*, MTT–30, No. 7, Jul. 1982.

"Radiofrequency–Induced Hyperthermia in the Prostate" by J. Scheiblich and O. Petrowicz, *Journal of Microwave Power*, 17 (3) 1982.

"Implantable Radiators for Cancer Therapy by Microwave Hyperthermia" by Leonard Taylor, *Proceedings of the IEEE*, vol. 68, No. 1, Jan. 1980.

"Microwave Applicators for Localized Hyperthermia Treatment of Cancer of the Prostate" by Jozef Mendecki, et al., *Technical Innovations and Notes, Radiation Oncology—Biology—Physics*, vol. 6, No. 11, Nov. 1980.

"Steady Magnetic Fields in Noninvasive Electromagnetic Flowmetry" by Sergio X. Salles–Cunha et al., *Proceedings of the IEEE*, vol. 68, No. 1, Jan. 1980.

"Microwave Applicators for Localized Hyperthermia Treatment of Malignant Tumors" by Mendecki et al., *Journal of Bioengineering*, vol. 1, 1977.

* cited by examiner

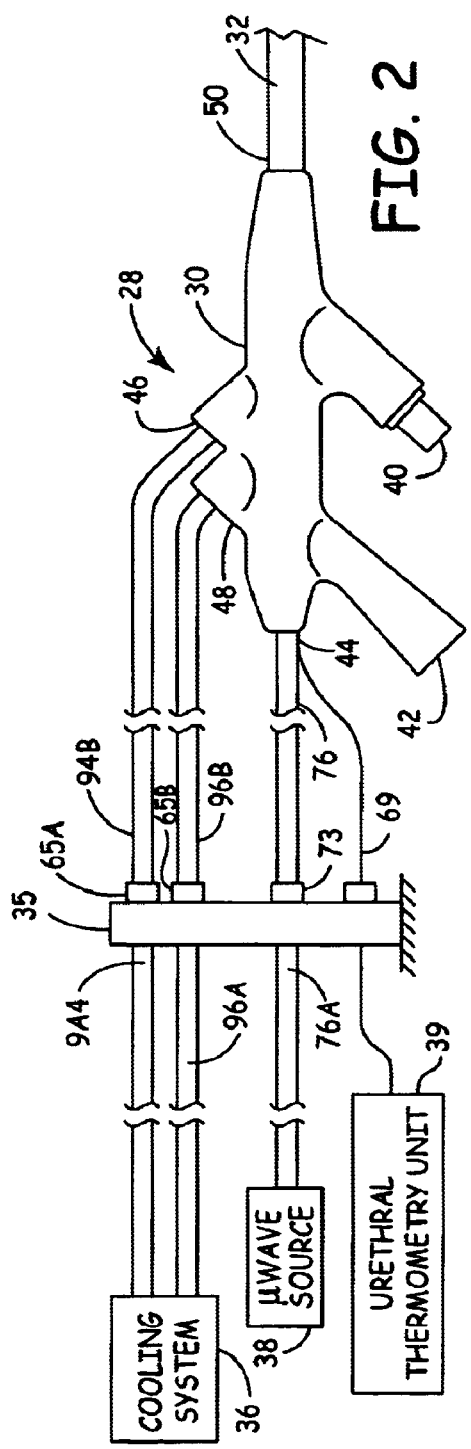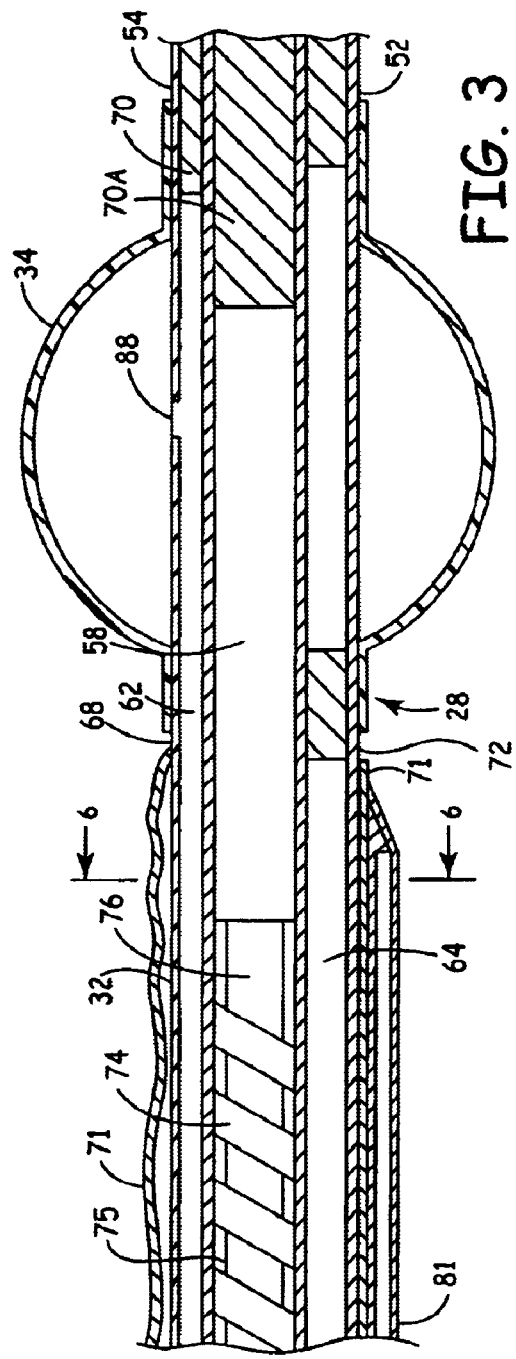

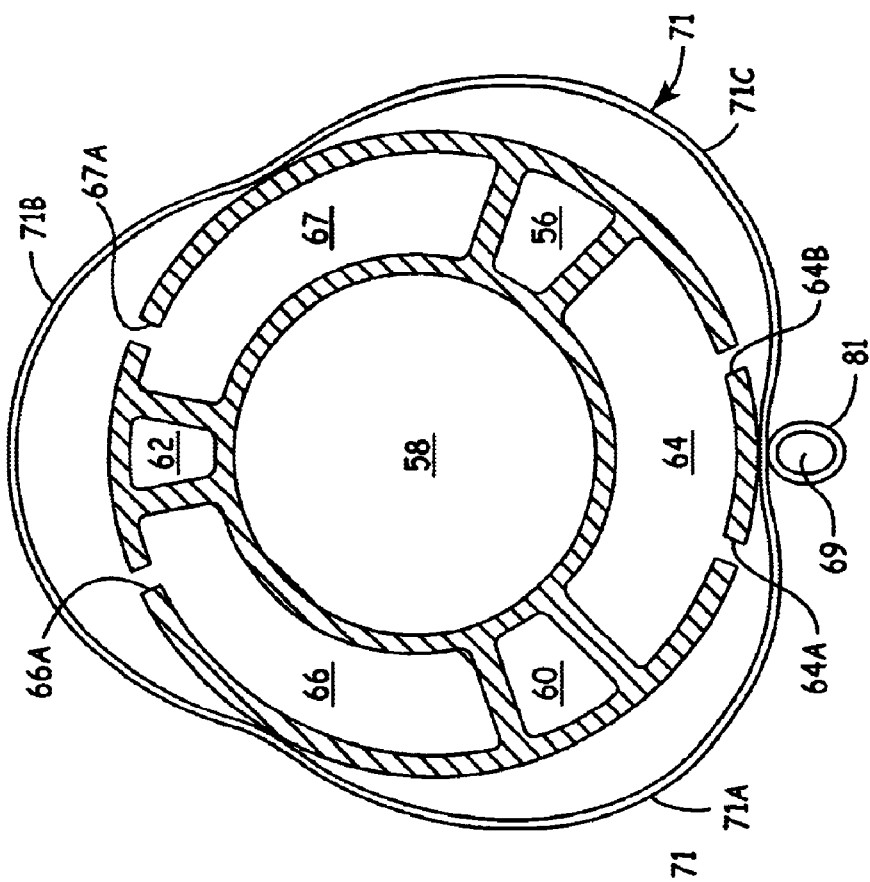
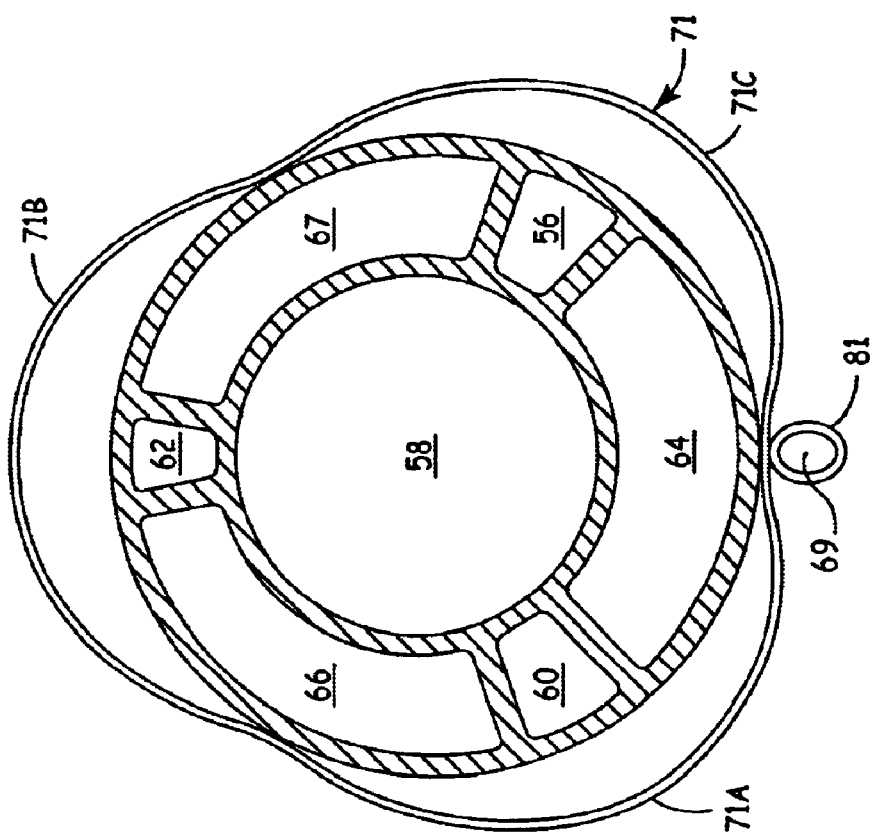

THERMAL TREATMENT CATHETER HAVING PREFERENTIAL ASYMMETRICAL HEATING PATTERN

CROSS-REFERENCE TO RELATED APPLICATION(S)

This application claims priority from Provisional Application No. 60/281,891 filed Apr. 5, 2001 for "Thermal Treatment Catheter Having Preferential Asymmetrical Heating Pattern" by D. Just, E. Rudie, J. Flachman, S. Stockmoe, A. Hjelle, B. Ebner, J. Crabb and S. Kluge.

BACKGROUND OF THE INVENTION

The present invention relates to a thermal treatment catheter, and more particularly to a catheter having a thin outer wall and a defined fluid flow path within the outer wall to improve the effects of conductive cooling of the wall of the body conduit in which the catheter is inserted. The catheter of the present invention also incorporates a microwave energy-attenuating strip within the catheter which serves to attenuate microwave energy generated by the catheter in the direction of non-treatment tissues.

The prostate gland is a complex, chestnut-shaped organ which encircles the urethra immediately below the bladder. Nearly one third of the prostate tissue anterior to the urethra consists of fibromuscular tissue that is anatomically and functionally related to the urethra and the bladder. The remaining two thirds of the prostate is generally posterior to the urethra and is comprised of glandular tissue. The portion of the urethra extending through the prostate (i.e., the prostatic urethra) includes a proximal segment, which communicates with the bladder, and a distal segment, which extends at an angle relative to the proximal segment by the verumontanum.

Although a relatively small organ, the prostate is the most frequently diseased of all internal organs and is often the site of a common affliction among older men, benign prostatic hyperplasia (BPH), as well as a more serious affliction, cancer. BPH is a nonmalignant, bilateral expansion of prostate tissue occurring mainly in the transition zone of the prostate adjacent to the proximal segment of the prostatic urethra. As this tissue grows in volume, it encroaches on the urethra extending into the region of the bladder neck at the base of the bladder. Left untreated, BPH causes obstruction of the urethra which usually results in increased urinary frequency, urgency, incontinence, nocturia and slow or interrupted urinary stream. BPH may also result in more severe complications, such as urinary tract infection, acute urinary retention, hydronephrosis and uraemia.

Benign prostatic hyperplasia (BPH) may be treated using transurethral thermal therapy as described in further detail in U.S. Pat. No. 5,413,588 entitled DEVICE AND METHOD FOR ASYMMETRICAL THERMAL THERAPY WITH HELICAL DIPOLE MICROWAVE ANTENNA and in U.S. Pat. No. 5,575,811 entitled BENIGN PROSTATIC HYPERPLASIA TREATMENT CATHETER WITH URETHRAL COOLING, both of which are hereby incorporated by reference. During transurethral thermal therapy, the transition zone of the prostate is heated to necrose the tumorous tissue that encroaches on the urethra. Transurethral thermal therapy is administered by use of a microwave antenna-containing catheter which includes a multi-lumen shaft. The catheter is positioned in the urethra with the microwave antenna located adjacent to the hyperplastic prostatic tissue. Energization of the microwave antenna causes the antenna to emit electromagnetic energy which heats tissue within the prostate. A cooling fluid is circulated through the catheter to preserve tissue such as the urethral wall between the microwave antenna and the target tissue of the prostate.

The commercially available Targis™ system from Urologix, Inc. of Minneapolis, MN employs a thermal therapy catheter that embodies the aforementioned U.S. Pat. No. 5,413,588, and is a product capable of performing thermal therapy of the prostate with microwave energy delivered from an applicator positioned in the urethra. The Targis™ system has achieved substantial clinical and commercial success, indicating the efficacy of microwave thermal therapy for treating prostate disease. The success of the Targis™ microwave thermal therapy system has led to continuing development efforts in the technology of thermal therapy catheters to further enhance the effects of microwave treatment of the prostate. One such development is disclosed in U.S. Pat. No. 6,161,049, entitled "THERMAL THERAPY CATHETER" by E. Rudie, S. Stockmoe, A. Hjelle, B. Ebner and J. Crabb, which is hereby incorporated by reference. A further development is the subject of the present invention.

BRIEF SUMMARY OF THE INVENTION

The present invention is a device and method for treating tissue adjacent to a body lumen such as a urethra. A catheter shaft having an outer surface is insertable into the body lumen, and the catheter shaft carries an energy-emitting element. The energy-emitting element is operable to radiate a generally symmetrical energy pattern. A plurality of cooling lumens in the catheter shaft around the energy-emitting element are configured for circulation of a fluid therethrough. An attenuating element is located in at least one of the plurality of cooling lumens. The attenuating element serves to attenuate energy in the direction of the non-treatment tissue, creating a radially asymmetrical thermal pattern in the tissue adjacent to the body lumen and thereby providing the capability to protect a designated region of healthy tissue from damaging amounts of thermal energy while permitting an increased depth of treatment of targeted tissues.

BRIEF DESCRIPTION OF THE DRAWINGS

FIG. 2 is a side view of the distal end of a thermal therapy catheter.

FIG. 3 is a section view of the proximal end of a thermal therapy catheter.

FIG. 5 is a section view of a thermal therapy catheter, taken along line 5—5 of FIG. 4.

FIG. 6 is a section view of a thermal therapy catheter, taken along line 6—6 of FIG. 3.

DETAILED DESCRIPTION

Figure 1:
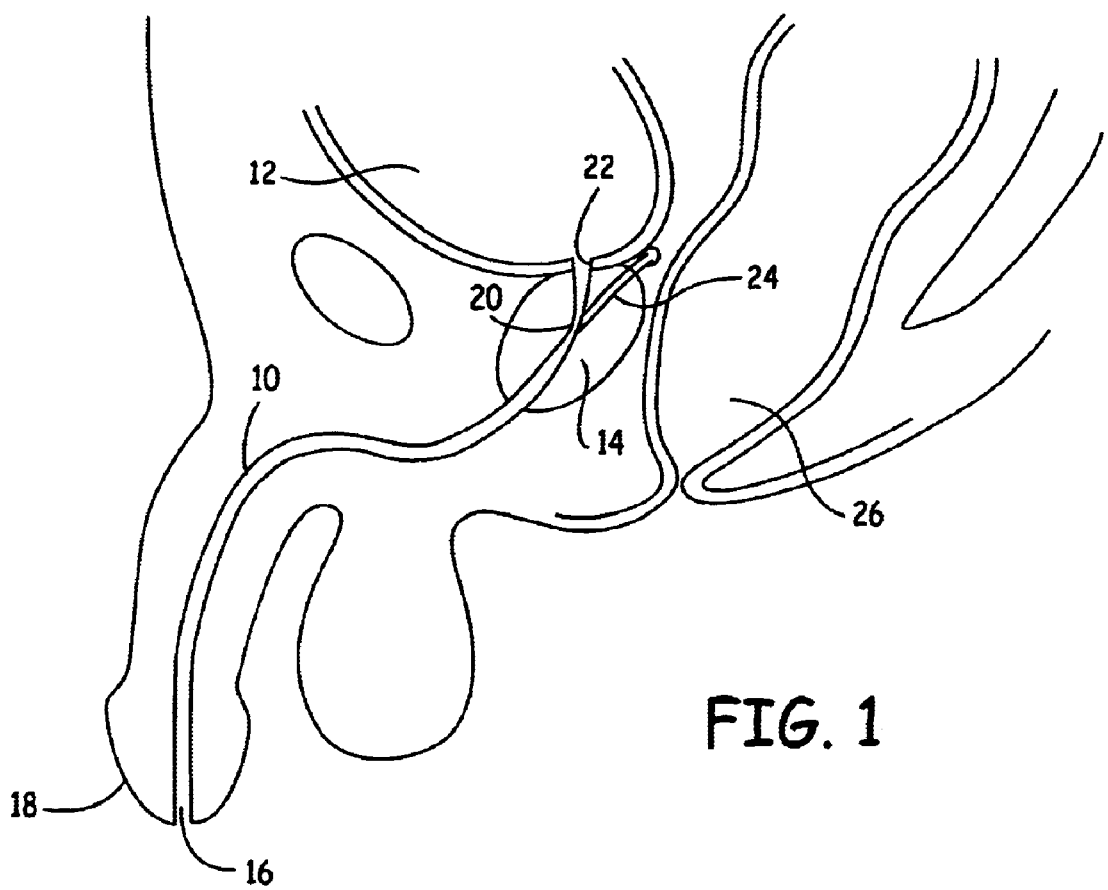
FIG. 1 is a vertical sectional view of a male pelvic region showing the urinary organs affected by benign prostatic hyperplasia.

FIG. 1 is a vertical sectional view of a male pelvic region showing the effect benign prostatic hyperplasia (BPH) has on the urinary organs. Urethra 10 is a duct leading from neck 22 of bladder 12, through prostate 14 and out orifice 16 of penis end 18. Benign tumorous tissue growth within prostate 14 around urethra 10 causes constriction 20 of urethra 10, which interrupts the flow of urine from bladder 12 to orifice 16. The tumorous tissue of prostate 14 which encroaches urethra 10 and causes constriction 20 can be effectively removed by heating and necrosing the encroaching tumorous tissue. Ideally, a selected volume of tissue of prostate 14 should be necrosed without harming adjacent healthy tissues such as urethra 10, bladder 12, ejaculatory duct 24 and rectum 26. The realization of this objective is enhanced by the microwave antenna-containing catheter of the present invention, which is shown in FIGS. 5–6.

FIGS. 2–6 relate to a thermal therapy catheter of U.S. Pat. No. 6,161,049, which is hereby incorporated by reference. FIG. 2 shows a side view of a distal end of catheter 28. Catheter 28 generally includes multi-port handle 30, multi-lumen shaft 32, shaft position retention balloon 34 (FIG. 3), connection manifold 35, cooling system 36, microwave generating source 38 and thermometry unit 39. Multi-port handle 30 includes inflation port 40, urine drainage port 42, microwave antenna port 44, cooling fluid intake port 46 and cooling fluid exit port 48. Ports 40–48 communicate with corresponding lumens within shaft 32. Handle 30 is preferably constructed as a two-piece snap-fit shell, composed of a thermoplastic elastomer or a similar material, with appropriate ports and channels being formed therein for communication with the lumens utilized by the thermal therapy catheter of the present invention.

Shaft 32 is connected to handle 30 at shaft distal end 50. Shaft 32 is a multi-lumen, Foley-type urethral catheter shaft. Shaft 32, which has an outer diameter of about 18 French, includes outer surface 52, which is generally circular in cross-section as shown in FIG. 5. Shaft 32 is both long enough and flexible enough to permit insertion of proximal shaft end 54 through urethra 10 into bladder 12 (FIG. 1). In a preferred embodiment, catheter shaft 32 is extruded from a thermoplastic elastomer. Thermoplastic materials are less expensive than medical-grade silicone, and are capable of being thermally processed, thereby obviating the need for adhesive bonding to the silicone, and the relatively long curing times associated therewith.

Figure 4:
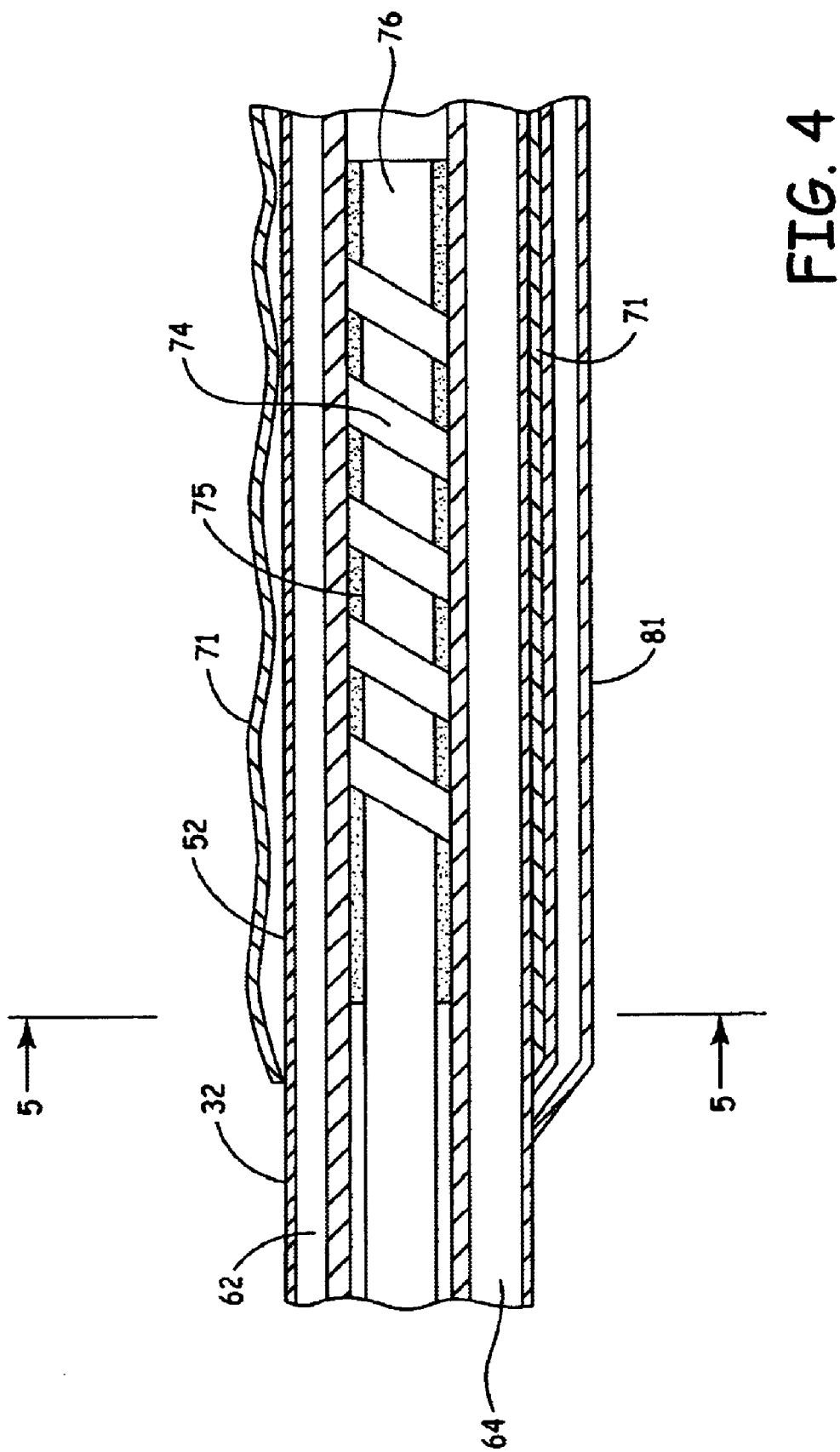
FIG. 4 is a section view of an intermediate portion of a thermal therapy catheter.

FIG. 3 is a section view of catheter shaft 32 adjacent proximal end 54 of shaft 32, and FIG. 4 is a section view of an intermediate portion of catheter shaft 32. Both FIG. 3 and FIG. 4 illustrate multi-lobe balloon 71 in its deflated state, for insertion of catheter 28 into urethra 10. FIG. 5 is a section view of catheter shaft 32 taken along line 5—5 of FIG. 4, and FIG. 6 is a section view of catheter shaft 32 taken along line 6—6 of FIG. 3. Both FIG. 5 and FIG. 6 illustrate multi-lobe balloon 71 in its inflated state, for operating to cool the wall of urethra 10 when microwave antenna 74 is energized.

As shown in FIGS. 3–6, shaft 32 generally includes temperature sensing fiber lumen 56, microwave antenna lumen 58, urine drainage lumen 60, balloon inflation lumen 62, cooling fluid intake lumen 64 and cooling fluid exhaust lumens 66 and 67. Lumens 56, 58, 60, 62, 64, 66 and 67 generally extend from distal shaft end 50 to proximal shaft end 54, and are located within catheter shaft 32 so as to form a catheter wall having uniform thickness throughout the cross-section of shaft 32, the catheter wall thickness being about 0.008 inches in an exemplary embodiment. Along the length of shaft 32, temperature sensing fiber lumen 56 communicates through the wall of shaft 32 through a channel formed in the catheter wall to temperature sensing fiber tube 81 attached to outer surface 52 of shaft 32. Temperature sensing fiber lumen 56, temperature sensing fiber tube 81 and the channel therebetween are sized to permit insertion of temperature sensing fiber 69 to monitor the temperature of tissue surrounding shaft 32 when it is inserted into urethra 10. Temperature sensing fiber 69 exits handle 30 through port 44 and is connected through manifold 35 to thermometry unit 39, which calculates temperature based on the optical information provided by temperature sensing fiber 69. Temperature sensing fiber lumen 56 has a generally trapezoidal cross-section, and together with the catheter walls on either side between cooling lumens 64 and 67 has an included angle of about 30.5 degrees. Multi-lobe balloon 71 is attached to outer surface 52 of shaft 32, preferably by thermal welding or a comparable attachment technique such as adhesive bonding, at one or more points on outer surface 52. Multi-lobe balloon 71 is preferably formed of a thermoplastic film wrapped around shaft 32, such as a polyurethane blown film in an exemplary embodiment. The construction and operation of multi-lobe balloon 71 is described in more detail with respect to FIG. 5.

In an exemplary embodiment, microwave antenna lumen 58 is located eccentric to the longitudinal axis of shaft 32, nearer first side 68 of shaft 32 than second side 72 of shaft 32. In the exemplary embodiment shown in FIGS. 5–6, the center of antenna lumen 58 is offset from the center of shaft 32 towards first side 68 of shaft 32 by 0.007 inches. Antenna lumen 58 is sealed at a proximal end of shaft 32 by plug 70A. At its distal end, microwave antenna lumen 58 communicates with microwave antenna port 44 (FIG. 2). Microwave antenna 74 is permanently positioned within antenna lumen 58 at the proximal end of shaft 32 near balloon 34. Antenna 74 is positioned within antenna lumen 58 so as to be generally situated adjacent the diseased tissue of prostate 14 when shaft 32 is properly positioned in urethra 10 with retention balloon 34 anchored at bladder neck 22. Antenna 74 includes wound coils carried at the proximal end of coaxial cable 76. The distal end of coaxial cable 76 is connected to manifold 35 by a conventional quick-coupling fitting 73. Coaxial cable 76 communicates with microwave generating source 38 by connection cable 76A, which is connected between microwave generating source 38 and manifold 35. In an exemplary embodiment, microwave antenna 74 is an impedance-matched antenna implemented in the manner generally disclosed in U.S. Pat. No. 5,413, 588, which has been incorporated herein by reference. It is also preferable for antenna lumen 58 and antenna 74 to have a relatively large radial dimension, about 0.131 inches in an exemplary embodiment, since a larger antenna radius results in lower transmission line losses and also provides greater column stiffness to facilitate insertion of shaft 32 into urethra 10. More specifically, because microwave antenna lumen 58 is located nearer first side 68 of shaft 32 than second side 70 of shaft 72, the orientation of shaft 32 in urethra 10 must be controlled to maximize the amount of energy delivered to tumorous tissue and minimize the amount of energy delivered to healthy tissue, such as the rectum, for example. Thus, microwave antenna 74 is designed to effectively transmit 100% of the torque applied to handle 30 on to the tip of shaft 32 at proximal end 54; that is, if handle 30 is rotated 20 degrees, the tip of shaft 32 at proximal end 54 also rotates 20 degrees. Microwave generating source 38 produces up to 100 watts of electrical power in an exemplary embodiment, in a frequency range of 902–928 MHZ, within the FCC-ISM standard range of frequencies. When antenna 74 is energized by microwave generating source 38, antenna 74 emits electromagnetic energy which causes heating of tissue within prostate 14.

In one preferred embodiment of the thermal therapy catheter of the present invention, a tip design may be used at proximal end 54 of catheter shaft 32 as described in U.S. Pat. No. 5,628,770 entitled DEVICES FOR TRANSURETHRAL THERMAL THERAPY, which is hereby incorporated by reference.

As shown in FIGS. 5–6, urine drainage lumen 60 is positioned adjacent antenna lumen 58, between antenna lumen 58 and lobe 71A of multi-lobe balloon 71. Urine drainage lumen 60 has a generally trapezoidal cross-section, and together with the catheter walls on either side between cooling lumens 64 and 66 has an included angle of about 30.5 degrees. Urine drainage lumen 60 communicates with urine drainage port 42 of handle 30 at distal shaft end 50 and defines a drainage path for urine when proximal end 54 of shaft 32 is inserted through urethra 10 into bladder 12. Urine drains from bladder 12 through urine drainage lumen 60 and out urine drainage port 42 when proximal shaft end 54 is inserted within bladder 12. Drainage of urine from bladder 12 is necessary due to frequent bladder spasms which occur during transurethral thermal therapy. Again, as mentioned above, in one preferred embodiment the tip design disclosed in U.S. Pat. No. 5,628,770, which has been incorporated by reference, may be used with catheter 28 of the present invention.

Retention balloon inflation lumen 62 is positioned adjacent antenna lumen 58, between antenna lumen 58 and lobe 71B of multi-lobe balloon 71. Balloon inflation lumen 62 has a generally trapezoidal cross-section, and together with the catheter walls on either size between cooling lumens 66 and 67 has an included angle of about 29 degrees. Balloon inflation lumen 62 communicates with inflation port 40 of handle 30 to allow inflation fluid to flow in and out of balloon inflation lumen 62, and communicates through aperture 88 to inflate retention balloon 34.

Cooling fluid intake lumen 64 is positioned adjacent to antenna lumen 58, between antenna lumen 58 and temperature sensing fiber tube 81 between lobes 71A and 71C of multi-lobe balloon 71. Cooling fluid intake lumen 64 has a generally arcuate cross-section, and extends from distal end 50 to proximal end 54 of shaft 32. Cooling fluid intake lumen 64 receives fluid from cooling system 36 to absorb a portion of the microwave energy emitted by the microwave antenna and thereby control the volume of prostatic tissue that is exposed to necrosing levels of heat. Fluid within cooling fluid intake lumen 64 also absorbs a portion of the heat energy generated by microwave energy from adjacent tissues via thermal conduction to avoid thermal damage to those tissues. In an exemplary embodiment, cooling fluid intake lumen 64 has an included angle of about 90 degrees.

Cooling fluid exhaust lumens 66 and 67 are positioned circumjacent to antenna lumen 58, with cooling fluid exhaust lumen 66 being located generally between antenna lumen 58 and lobes 71A and 71B of multi-lobe balloon 71 and cooling fluid exhaust lumen 67 being located generally between antenna lumen 58 and lobes 71B and 71C of multi-lobe balloon 71. Cooling fluid exhaust lumens 66 and 67 have a generally arcuate cross-section, and extend from distal end 50 to proximal end 54 of shaft 32. Exhaust lumens 66 and 67 provide a return path to cooling system 36 for fluid circulated through intake lumen 64 and multi-lobe balloon 71. Fluid within exhaust lumens 66 and 67 absorbs a portion of the microwave energy emitted by the microwave antenna and also absorbs a portion of the heat energy generated by microwave energy from adjacent tissues via thermal conduction, in the manner described above. In an exemplary embodiment, cooling fluid exhaust lumens 66 and 67 each have an included angle of about 90 degrees.

FIG. 6 is a section view of catheter shaft 32 taken along line 6—6 of FIG. 3. As shown in FIG. 6, at proximal end 54 of shaft 32 cooling lumens 64, 66 and 67 communicate with the interior of multi-lobe balloon 71 so as to provide cooling fluid to inflate multi-lobe balloon 71. Specifically, cooling fluid intake lumen 64 communicates with the interior of lobe 71A through aperture 64A and communicates with the interior of lobe 71C through aperture 64B. Cooling fluid exhaust lumen 66 communicates with the interior of lobe 71B through aperture 66A, and cooling fluid exhaust lumen 67 communicates with the interior of lobe 71B through aperture 67A. Cooling fluid intake lumen 64 and exhaust lumens 66 and 67 cooperate with cooling system 36 via ports 46 and 48 of handle 30 to provide a selectively controlled flow of fluid through cooling lumens 64, 66 and 67 during a treatment session. In operation, cooling fluid flows from cooling system 36 to cooling fluid feed line 94B and on through port 46 of handle 30 into cooling fluid intake lumen 64. The cooling fluid continues to flow under dynamic fluid pressure through apertures 64A and 64B to inflate lobes 71A and 71C of multi-lobe balloon 71. Cooling fluid flows from lobe 71B through apertures 66A and 67A into cooling fluid exhaust lumens 66 and 67, and exits shaft 32 at distal end 50 thereof through port 48 of handle 30, and on through cooling fluid return line 96B and manifold 35 to cooling system 36 for re-chilling and recirculation. Cooling fluid feed line 96B and return line 96B are each provided with a conventional quick-coupling fitting 65A and 65B, respectively, which permits catheter 28 to be easily disconnected from cooling system 36. In an exemplary embodiment, the cooling fluid is deionized water provided by cooling system 36, chilled to an appropriate temperature so as to maintain the temperature of tissue immediately surrounding catheter shaft 32 at a predetermined value while power is applied from microwave antenna 74 to heat diseased prostate tissue. A method of controlling coolant temperature and microwave power to maintain a predetermined tissue temperature is disclosed in U.S. Pat. No. 6,122,551, entitled "METHOD OF CONTROLLING THERMAL THERAPY," which is hereby incorporated by reference. The water is pumped at a rate sufficient to provide dynamic pressure to inflate multi-lobe balloon 71 to create an outer balloon diameter of about 24 French, thereby ensuring excellent wall contact with the urethra and enhancing the efficiency of the conductive cooling performed by the circulating cooling fluid flowing in multi-lobe balloon 71.

Figure 7:
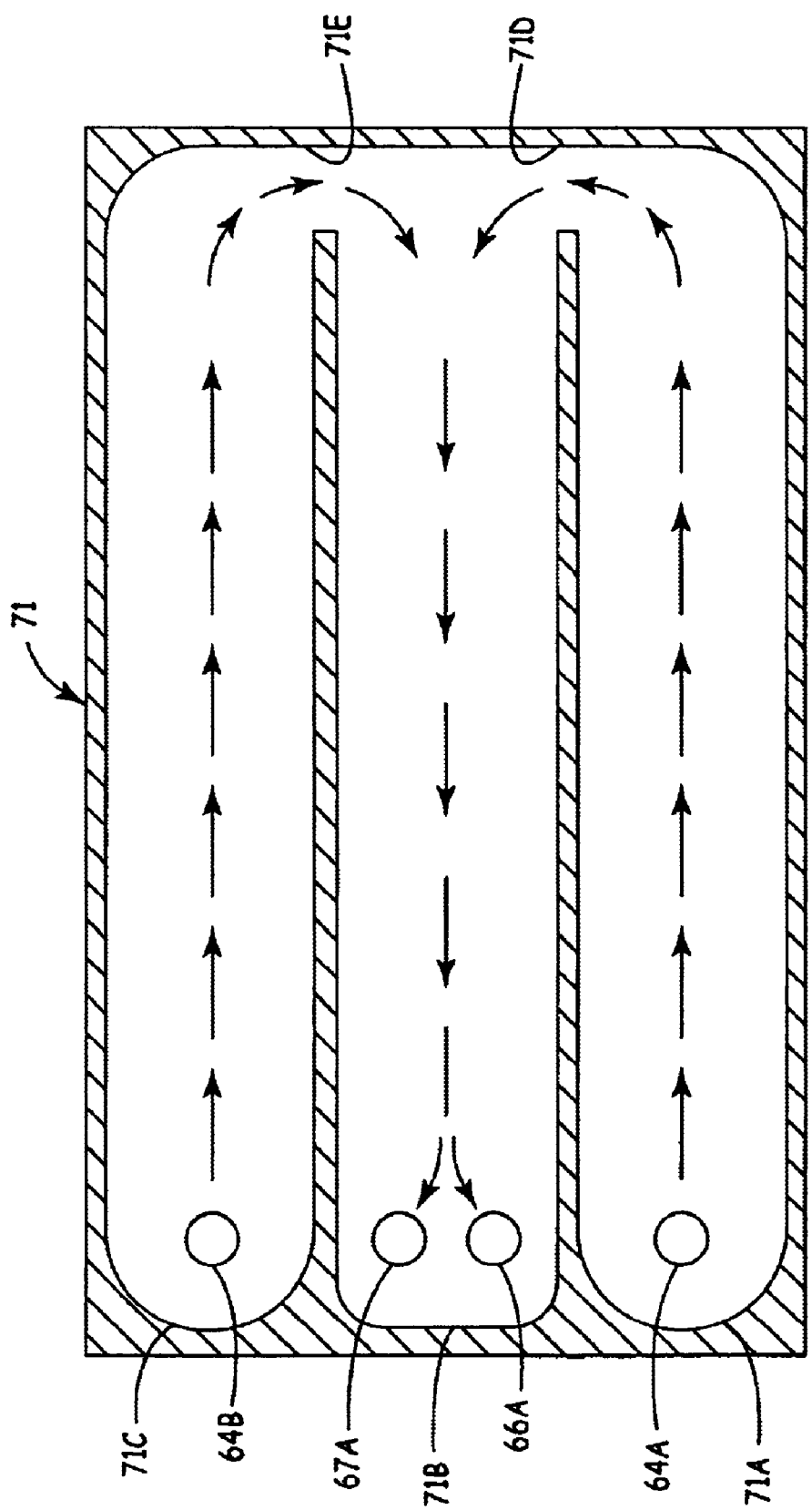
FIG. 7 is a diagram illustrating the flow path of cooling fluid through the multi-lobe balloon of a thermal therapy catheter.

FIG. 7 illustrates the pattern of fluid flow through multi-lobe balloon 71 according to an embodiment of the present invention. For the purpose of illustration, multi-lobe balloon 71 is shown in FIG. 7 as "flattened out" in two dimensions; it should be understood that multi-lobe balloon 71 is wrapped around catheter shaft 32 in a final assembly of the present invention, as shown in the cross-sectional views of FIGS. 5 and 6. The cross-hashed regions of balloon 71 indicate where balloon 71 is thermally welded (or otherwise attached) to the catheter shaft, with the patterns of multi-lobe balloon 71 being formed by heat stamping or an alternative processing method. Cooling fluid is circulated into lobe 71A of multi-lobe balloon 71 through fluid flow aperture 64A and into lobe 71C of multi-lobe balloon 71 through fluid flow aperture 64B. The cooling fluid flows under dynamic pressure in the direction indicated by the arrows, through narrow channels 71D and 71E into lobe 71B of multi-lobe balloon 71, where the fluid exits through fluid flow apertures 66A and 67A into exhaust lumens 66 and 67 of shaft 32. The fluid flow path provided by the present invention ensures that the cooling fluid circulates under sufficient dynamic pressure to inflate multi-lobe balloon 71 to a sufficient diameter to provide consistent wall contact with the urethra, such as about 24 French in an exemplary embodiment. More complex flow patterns in the lobes of balloon 71 are also contemplated by the present invention, which may be realized by heat stamping and thermal welding processes, or alternatively by adhesive bonding processes, to form the appropriate flow pattern. In addition, multi-lobe balloon 71 may be formed with more than the three lobes 71A, 71B and 71C illustrated in FIGS. 5 and 6, thereby forming modifying the fluid flow pattern and inflation characteristics of balloon 71. The actual amount of dynamic fluid flow pressure may be controlled by adjusting a number of parameters, such as the rate at which cooling fluid is pumped from the cooling system, the width of channels 71D and 71E, the size of fluid flow apertures 64A, 64B, 66A and 67A, the width of restricted flow areas elsewhere in the fluid flow path, and other parameters that will be apparent to one skilled in the art. In an exemplary embodiment, dynamic fluid pressure is controlled by an adjustable restrictor located in the fluid flow path proximate to cooling system 36.

A thermal therapy catheter as described above is designed to enhance the efficiency of treatment of diseased tissue from an adjacent body lumen, particularly for treatment of diseased prostate tissue from a urethrally inserted applicator. A multi-lobe balloon is attached around the catheter shaft, with interiors of the balloon lobes in communication with cooling lumens of the catheter, so that circulation of fluid in the cooling lumens dynamically inflates the balloon lobes. The radial spacing and shaping of lobes 71A, 71B and 71C are designed to define a fluid chamber that corresponds to the generally triangular cross-sectional geometry of the urethra. As a result, the balloon lobes more readily come into intimate contact with the wall of the urethra, and the cooling fluid circulating in the balloon lobes is thereby able to efficiently conduct heat away from the urethral wall tissue to preserve the urethra while delivering microwave energy to heat prostate tissue to high temperatures (above about 45° C.) for a sufficient time to necrose the targeted prostate tissue. In one embodiment, the balloon wall thickness is about 0.002 inches. In addition, the inflatable nature of the multi-lobe cooling balloon allows the catheter to be easily inserted when the balloon is not inflated (with the catheter shaft having a relatively small diameter of about 18 French) while providing the ability to firmly contact the urethral wall to enhance cooling when the balloon is inflated, up to a diameter of about 24 French in one embodiment.

The arrangement and shape of the lumens in the catheter shaft is also designed for efficient operation of the thermal therapy catheter system. As shown in FIGS. 5 and 6, temperature sensing fiber lumen 56, urine drainage lumen 60 and balloon inflation lumen 62 are all formed with generally trapezoidal cross-sections, so as to minimize the included angle of each of these lumens. As a result, the included angle of cooling lumens 64, 66 and 67 is maximized, improving the efficiency of urethral cooling. In addition, the seams which define lobes 71A, 71B and 71C of multi-lobe balloon 71 correspond with cooling lumens 64, 66 and 67, which ensures that sufficient cooling of the urethral wall occurs at the seams of multi-lobe balloon 71 in addition to the inflated lobes of the balloon. Cooling lumens 64, 66 and 67 also extend along the entire length of the microwave antenna to provide internal cooling of the catheter and thereby ensure that the thermoplastic material of the catheter shaft is not melted by the resistive heating produced by the antenna and the heating produced by absorption of microwave energy by the catheter walls.

Temperature sensing fiber 69 within temperature sensing fiber tube 81 is also strategically placed in the catheter design. Temperature sensing fiber tube 81 is located in the seam between lobes 71A and 71C of multi-lobe balloon 71, so as to minimize its effect on the outer perimeter shape of the catheter. In addition, the location of temperature sensing fiber tube 81 also ensures that cooling lumen 64 is positioned directly between temperature sensing fiber 69 and the microwave antenna positioned in antenna lumen 58. As a result, the resistive heating produced by the microwave antenna has no appreciable effect on the temperature reading obtained by temperature sensing fiber 69; the only variables that affect the temperature reading are the actual temperature of tissue immediately adjacent temperature sensing fiber tube 81 and the temperature of the cooling fluid circulating through cooling lumen 64. The cooling fluid temperature may be compensated for by the thermometry unit to yield an accurate value for the actual tissue temperature, which is useful information for controlling the thermal therapy procedure.

As a result of the above-described catheter design and the efficient cooling of the body lumen wall provided by the multi-lobe balloon, a substantial depth of tissue may be heated above about 45° C. for a time sufficient to necrose the tissue, while protecting the body lumen wall from thermal damage. Under the regulation of an effective control algorithm, such as is disclosed in the aforementioned U.S. Pat. No. 6,122,551, which has been incorporated herein by reference, the catheter design of the present invention is able to necrose a substantial portion of the prostate while controlling temperatures to protect healthy tissues such as the urethral wall and the rectum, with a treatment time of approximately 30 minutes or less and no need for anesthesia. The system therefore offers an attractive therapy option for treating tissue disease such as BPH, with excellent long-term results and a low risk of morbidity or other side effects.

Figure 8:
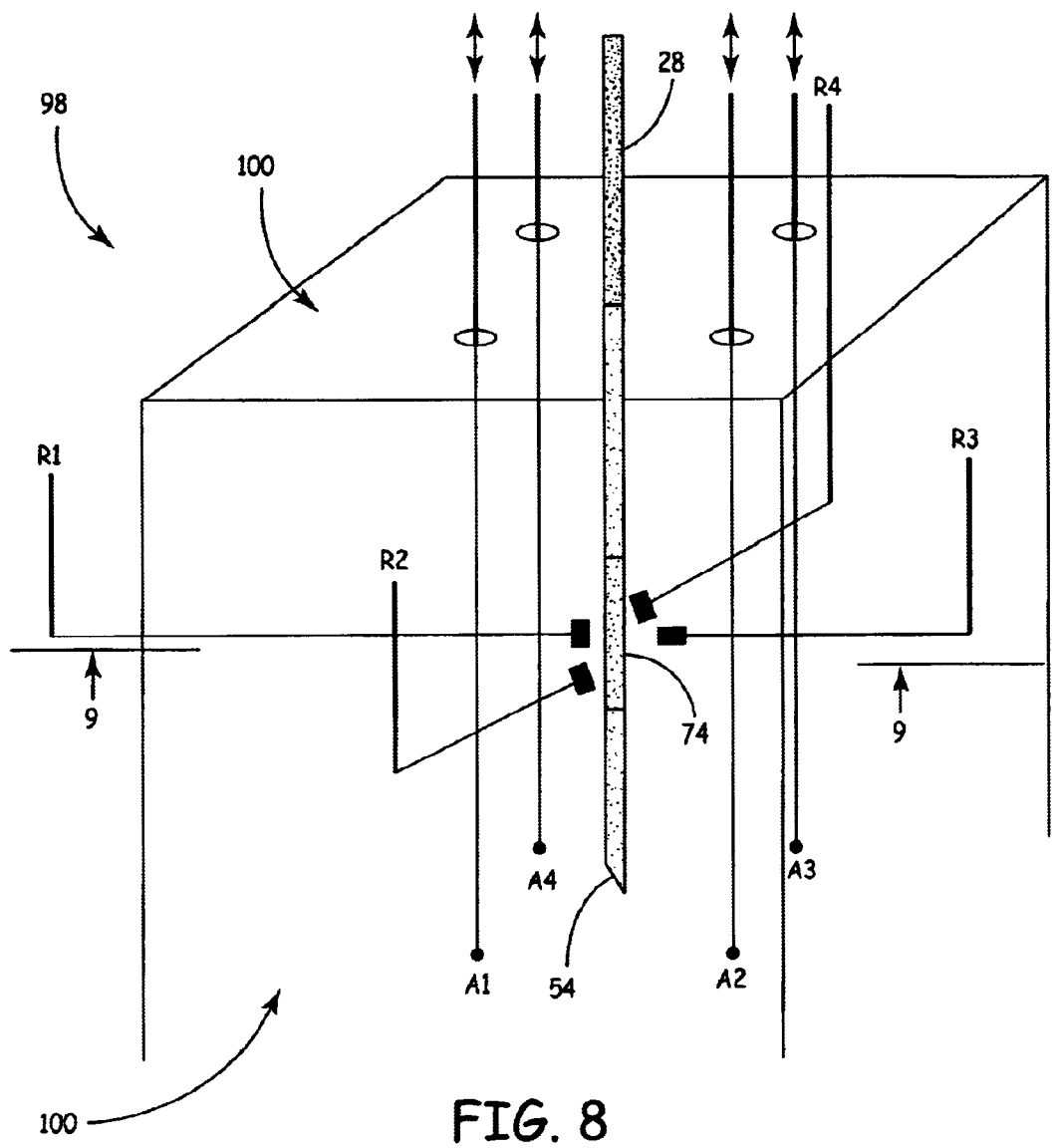
FIG. 8 is a perspective view of the testing system used to measure the temperature distribution of the thermal therapy catheter of FIGS. 5–6 and of the present invention.

FIG. 8 is a perspective view of testing system 98 in which basic performance characteristics concerning energy and temperature distribution patterns capable of being achieved by the catheter of FIGS. 5–6 are demonstrated. As shown diagrammatically in FIG. 8, proximal end 54 of catheter 28 is inserted into a block of gelatinous phantom tissue medium 100 composed primarily of distilled water, ethylene glycol and sodium chloride. Tissue medium 100 is held in place by a cubicle container having six transparent, plastic walls. Catheter 28 is positioned in the tissue medium 100 by vertically inserting catheter 28 through a pre-positioned channel (not shown) in tissue medium 100 so that catheter 28 is located in the center of tissue medium 100. Four radially movable temperature sensors R1, R2, R3 and R4 are located within four pre-positioned channels (not shown) in tissue medium 100 in a common plane, which is transverse to a vertical plane defined by catheter 28. Catheter 28 is positioned relative to temperature sensors R1–R4 such that a midpoint of microwave antenna 74 is adjacent to temperature sensors R1–R4. Temperature sensors R1–R4 are capable of radial movement in unison away from catheter 28, with a starting position of each sensor being located about 0.5 cm from catheter 28. Temperature sensors R2 and R3 are located on opposite sides of catheter 28 and move radially away from each other. Temperature sensors R1 and R4 are also located on opposite sides of catheter 28 and move radially away from each other. Through this configuration, temperature sensors R1–R4 are equally radially spaced from each other around catheter 28.

Four axially movable temperature sensors A1, A2, A3 and A4 are located within four pre-positioned channels (not shown) in tissue medium 100. Temperature sensors A1–A4 are located adjacent to a longitudinal axis of catheter 28, and are capable of axial movement in unison along the length of catheter 28. Each temperature sensor A1–A4 is located an axial distance of 0.5 cm from catheter 28. Temperature sensors A1–A4 are equally radially spaced around catheter 28 in order to capture temperature readings on discrete sides of catheter 28. At the start of a testing procedure, temperature sensors A1–A4 are aligned in a common horizontal plane located below proximal end 54 of catheter 28. During a testing procedure, temperature sensors A1–A4 move axially upwards along the length of antenna 74 of catheter 28.

Figure 8A:
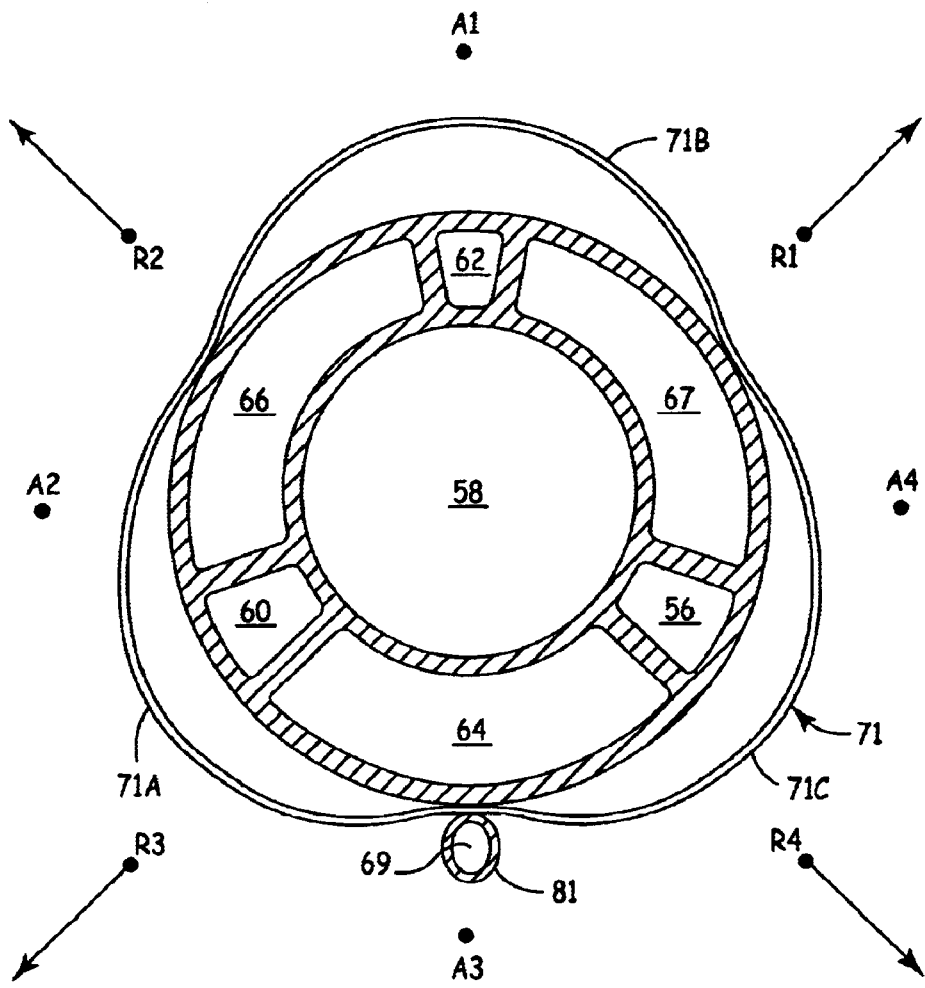
FIG. 8A is an enlarged a section view of the testing system taken along line 9—9 of FIG. 8.

FIG. 8A shows a cross-sectional view of the testing system of FIG. 8 taken along line 9—9. FIG. 8A shows the orientation of the temperature sensors R1–R4 and A1–A4 relative to catheter 28 and microwave antenna 74. Temperature sensors R1–R4 are shown in their starting position for a test phase. The directions of movement for temperature sensors R1–R4 are illustrated by the arrows in FIG. 8A.

An exemplary testing procedure using testing system 98 is composed of multiple testing phases, each testing phase lasting approximately 1.2 minutes. Testing phases may be performed at 5 and 10 minutes during a testing procedure, for example. During a testing phase, the movement of the temperature sensors R1–R4 and A1–A4, and the recording of temperatures in tissue medium 100 are computer controlled by testing system 98. Before a testing procedure begins, tissue medium 100 typically has a temperature of about 25° C. and catheter 28 typically has a temperature of about 25.3° C. Microwave antenna 74 of catheter 28 is energized to a power level of 30 watts at a frequency of 927 Hertz at the start of a testing procedure.

During each testing phase, temperature sensors R1–R4 begin at their start positions 0.5 cm from catheter 28 and move in radial directions shown in FIG. 8A away from catheter 28 to a distance of about 60 mm. As temperature sensors R1–R4 move through tissue medium 100, the temperature sensors measure the temperature of tissue medium 100. A temperature recording is taken at 2.5 mm increments in tissue medium 100. After a testing phase is completed, the temperature sensors R1–R4 are repositioned in their start positions in preparation for the following testing phase. Temperature sensors R1–R4 move at a constant rate of about 0.8 mm per second during each testing phase of the testing procedure.

Temperature sensors A1–A4 begin each testing phase at a location proximal of antenna 74. Throughout a testing phase, temperature sensors A1–A4 maintain a constant radial distance of 0.5 cm away from catheter 28 as temperature sensors A1–A4 move adjacent to the longitudinal axis of catheter 28. Temperature sensors A1–A4 pass along a section of catheter 28 containing microwave antenna 74 during a testing phase, and the temperature sensors end each testing phase at a location distal of microwave antenna 74. Temperature sensors A1–A4 record a temperature of tissue medium 100 every 2.5 mm during a testing phase. Once a testing phase is complete, temperature sensors A1–A4 are repositioned in their starting locations in preparation for a following testing phase. Temperature sensors A1–A4 move at a constant rate of about 0.8 mm per second during each testing phase of the testing procedure, in coordination with the movement of sensor R1–R4.

Figure 9:
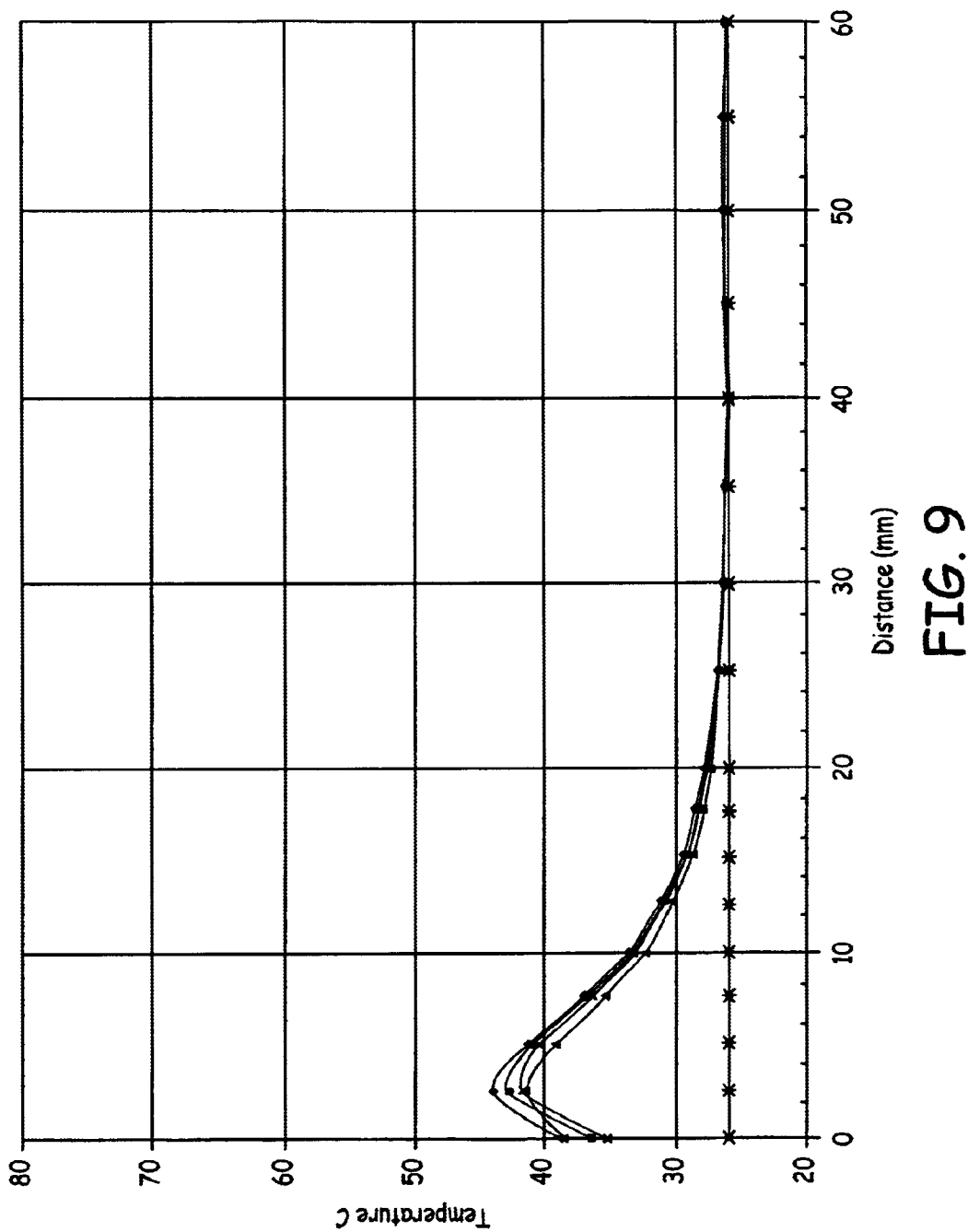
FIG. 9 is a graph showing the temperature of phantom tissue due to operation of the thermal therapy catheter of FIGS. 5–6 as a function of radial distance from the catheter, taken at 5 minutes into a testing procedure using the testing system of FIG. 8.
Figure 10:
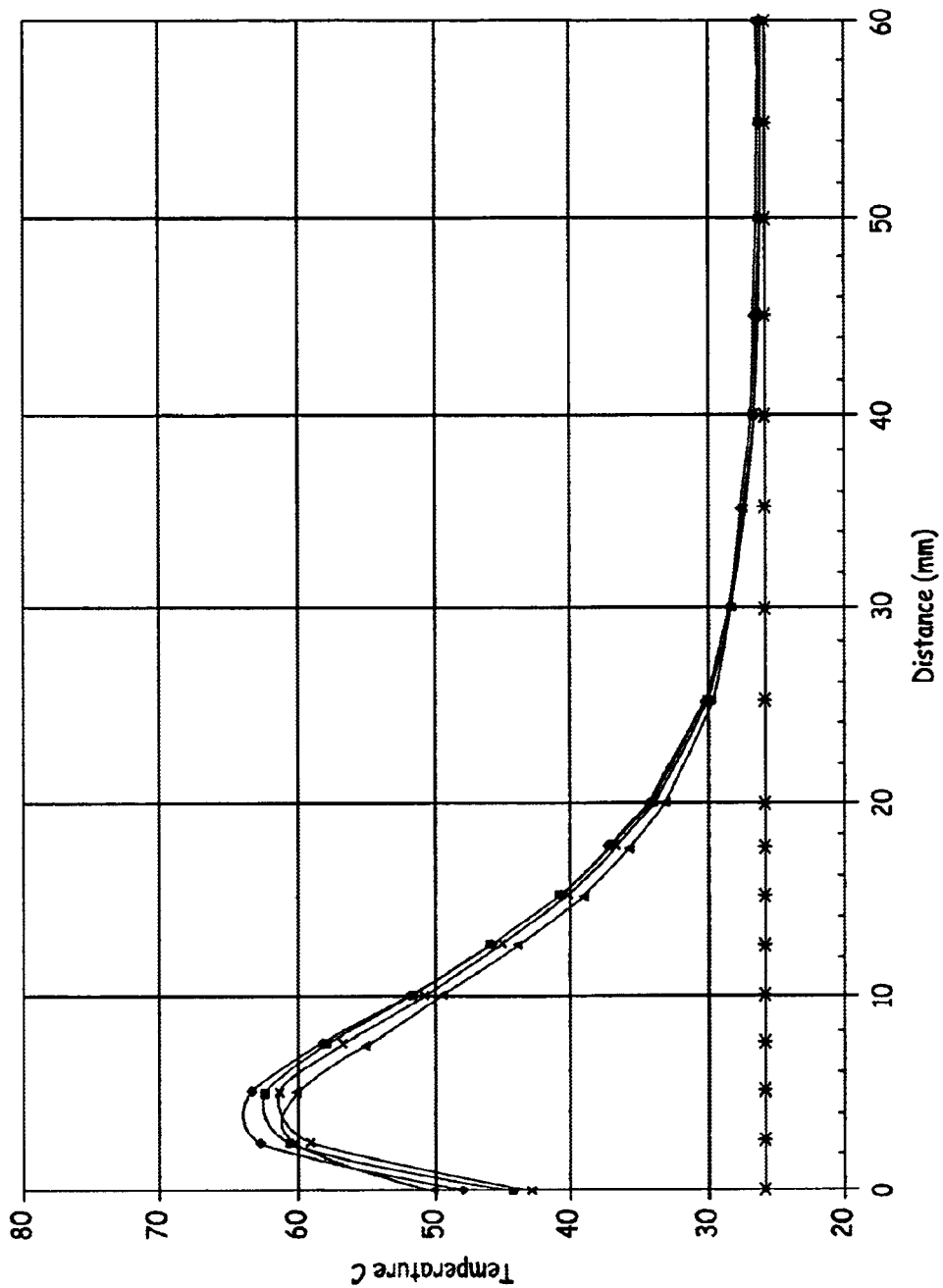
FIG. 10 is a graph showing the temperature of phantom tissue due to operation of the thermal therapy catheter of FIGS. 5–6 as a function of radial distance from the catheter, taken at 10 minutes into a testing procedure using the testing system of FIG. 8.

FIGS. 9–10 show temperature recordings of temperature sensors R1–R4 in comparison to the distances of temperature sensors R1–R4 from catheter 28 during a complete testing procedure. FIGS. 9–10 each represent temperature and distance data from a single testing phase. The vertical axes of FIGS. 9–16 correspond to the temperature of tissue medium 100, and the horizontal axes correspond to the radial distance away from catheter 28 of temperature sensors R1–R4. In FIGS. 9–10, temperature recordings of R1 are shown by diamond marks, temperature recordings of R2 are shown by square marks, temperature recordings of R3 are shown by triangle marks, and temperature recordings of R4 are shown by "x" marks. FIGS. 9–10 show that temperature sensors R1–R4 record substantially similar temperatures at similar locations in tissue medium 100 throughout each testing phase. Thus, FIGS. 9–10 illustrate that catheter 28 produces a radially symmetrical temperature distribution in tissue medium 100. Also, FIGS. 9–10 show that temperature of tissue medium 100 steadily increases during a testing procedure, and that a similar temperature distance pattern is developed during each testing phase.

FIGS. 9–10 show the temperature recordings of temperature sensors R1–R4 during a testing phase performed at 5 and 10 minutes, respectively, into the testing procedure. FIGS. 9–10 show an initial temperature increase as temperature sensors R1–R4 move radially away from catheter 28. After reaching peak temperatures ranging from about 40° C. to 70° C. (with the higher peak temperatures occurring after phantom tissue medium 100 has been exposed to the emitted energy for a longer period of time), temperatures sensors R1–R4 show a steady decrease in temperature as temperature sensors R1–R4 move further away from catheter 28. FIGS. 9–10 illustrate that temperature sensors R1–R4 are recording generally similar temperatures at similar distances away from catheter 28 for each respective test, with only slightly lower temperatures being measured in tissue adjacent to balloon lobes 71A and 71C, as reflected by the curves for sensors R3 and R4. Thus, FIGS. 9–10 show that catheter 28 is generating a substantially uniform temperature distribution radially throughout tissue medium 100 after microwave antenna 74 has been energized.

Figure 11:
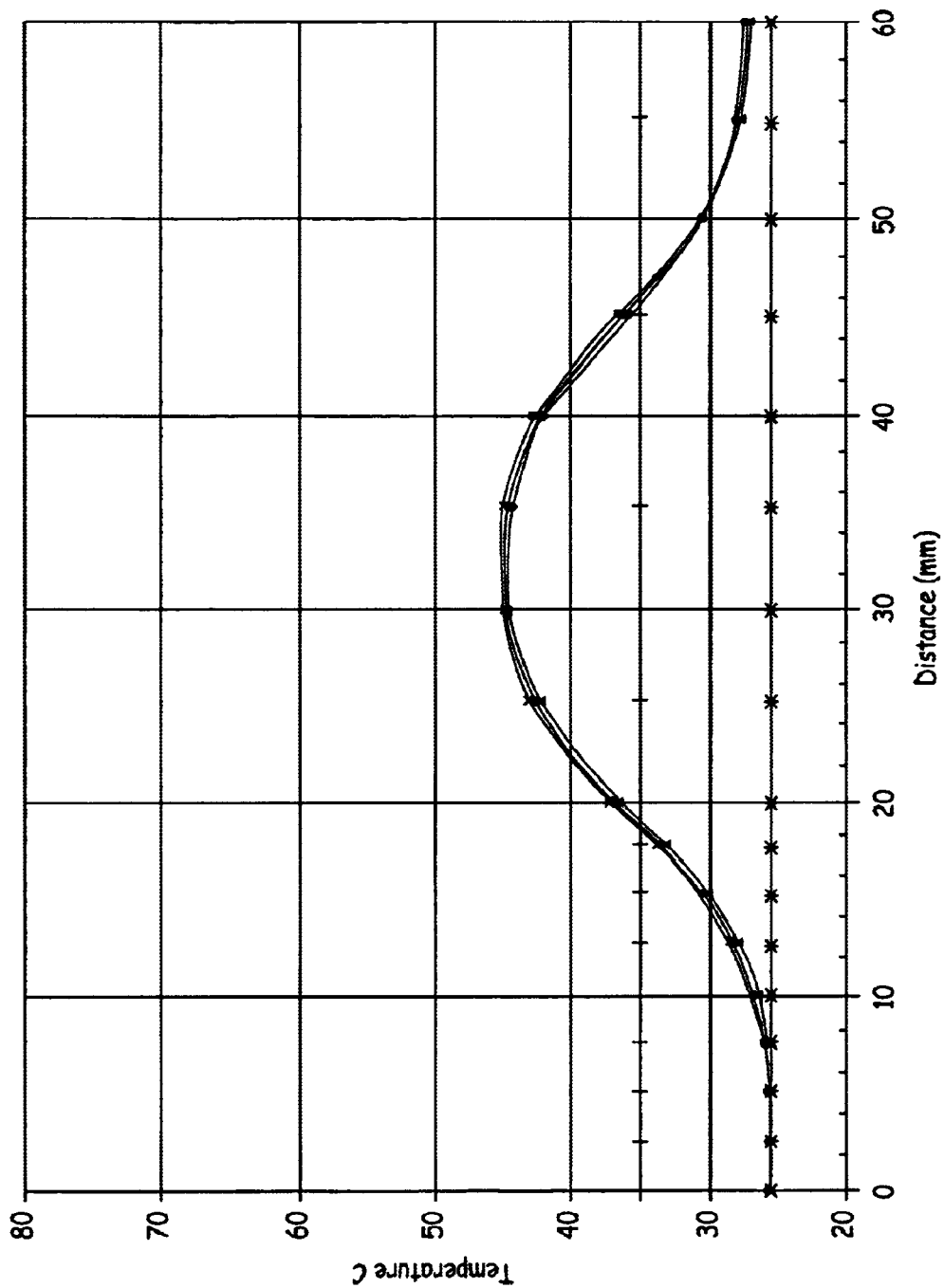
FIG. 11 is a graph showing an axial distribution of temperature in phantom tissue relative to the energy-emitting element of the thermal therapy catheter of FIGS. 5–6 during operation of the catheter, taken at 5 minutes into a testing procedure using the testing system of FIG. 8.
Figure 12:
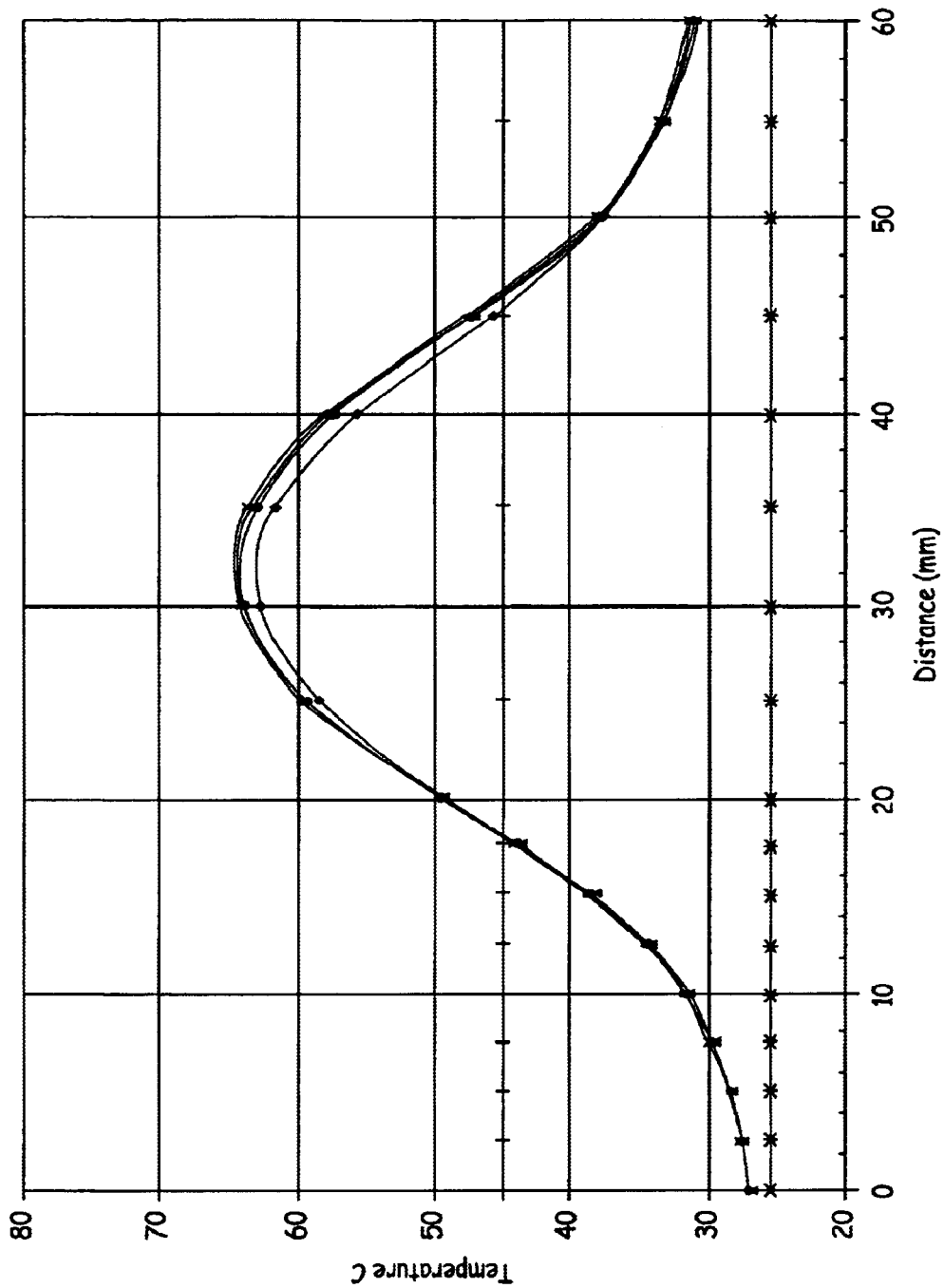
FIG. 12 is a graph showing an axial distribution of temperature in phantom tissue relative to the energy-emitting element of the thermal therapy catheter of FIGS. 5–6 during operation of the catheter, taken at 10 minutes into a testing procedure using the testing system of FIG. 8.

FIGS. 11–12 show the temperature recordings of temperature sensors A1–A4 in comparison to the positions of temperature sensors A1–A4 along the length of catheter 28 during a complete testing procedure. FIGS. 11–12 each represent temperature and distance data from a single testing phase, at 5 and 10 minutes into a testing procedure, respectively. The vertical axes of FIGS. 11–12 correspond to the temperature of tissue medium 100, and the horizontal axes correspond to the axial distance along catheter 28 of temperature sensors A1–A4. In FIGS. 11–12, temperature recordings of A1 are shown by diamond marks, temperature recordings of A2 are shown by square marks, temperature recordings of A3 are shown by triangle marks, and temperature recordings of A4 are shown by "x" marks. FIGS. 11–12 show that temperature sensors A1–A4 record substantially similar temperatures at similar locations along catheter 28 in tissue medium 100 throughout each testing phase. Thus, FIGS. 11–12 illustrate that catheter 28 produces a generally radially symmetrical temperature distribution along catheter 28, with the intensity of energy and therefore the measured temperature increasing as a function of time.

FIGS. 9–10 display the temperature data recorded by temperature sensors R1–R4 throughout a complete testing procedure. Note that FIGS. 9–10 show a similar pattern for temperature variation (a gradual increase and then a decrease) as temperature sensors R1–R4 move radially away from catheter 28. Also note that temperature sensors R1–R4 are recording similar temperatures at similar distances away from the catheter, even though temperature sensors R1–R4 are moving in four separate directions relative to four different sides of catheter 28. Thus, FIGS. 9–10 illustrate that catheter 28 generates a radially symmetrical temperature distribution in tissue medium 100 surrounding catheter 28.

FIGS. 11–12 display the temperature data recorded by temperature sensors A1–A4 throughout a complete testing procedure. Similar to temperature sensors R1–R4, temperature sensors A1–A4 show a symmetrical heating distribution in all radial directions from catheter 28 in tissue medium 100. Thus, FIGS. 9–10 in combination with FIGS. 11–12 confirm that catheter 28 generates a generally radially symmetrical heating pattern throughout tissue medium 100.

Microwave thermal therapy such as is described above may be further enhanced with the present invention to maximize the amount of energy emitted toward targeted tissues while controlling the energy emitted toward certain healthy tissues to avoid thermal damage to those tissues. The rectum, for example, contains tissue that is susceptible to thermal damage. The radial extent of necrosis produced by a catheter emitting a symmetrical heating pattern is limited by the close proximity of the rectum relative to the urethra. While a control algorithm may be utilized to limit power to the microwave antenna so as to protect the rectum from thermal damage, modifying the thermal treatment catheter to restrict the amount of energy delivered toward the rectum enhances the ability to effectively necrose the greatest possible volume of diseased prostate tissue without thermally damaging the rectum. A catheter system achieving this objective and associated test results are disclosed in FIGS. 13–18. Clinicians using the nonuniform heat-distributing catheter system of the present invention can position the catheter within a body cavity in such a manner that tissues designated for treatment are exposed to high amounts of thermal energy while healthy tissues are exposed to lower, non-damaging amounts of thermal energy.

Figure 13:
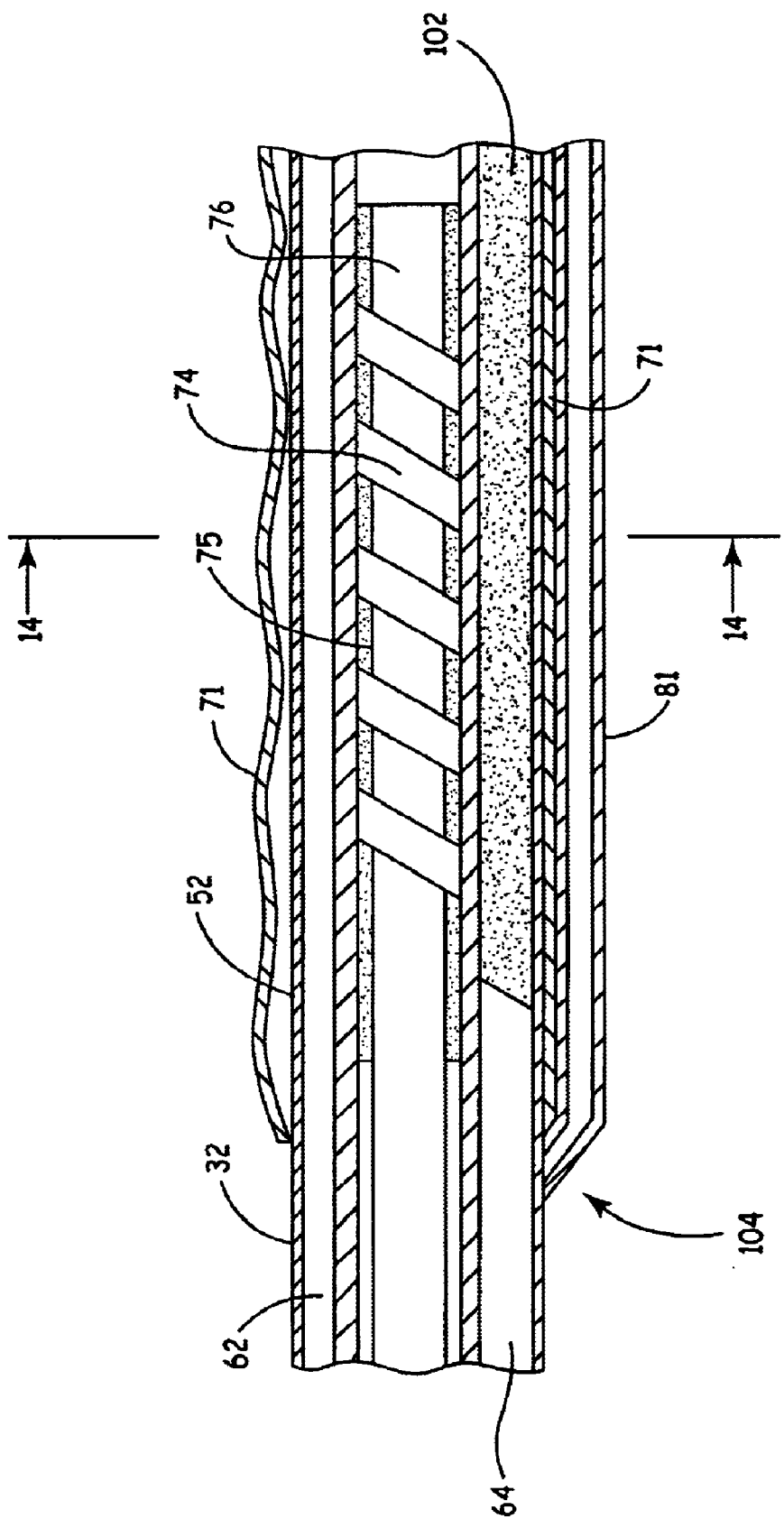
FIG. 13 is a longitudinal sectional view of the thermal therapy catheter of the present invention.

FIG. 13 is a side view of one preferred embodiment of a catheter of the present invention. Catheter 104 incorporates all of the previously-described features of catheter 28 shown FIGS. 2–7. Additionally, catheter 104 includes metal strip 102 composed of a material such as brass, for example, located in cooling lumen 64 of catheter 104. Metal strip 102 has a length at least corresponding to the length of microwave antenna 74, and serves to alter the microwave energy pattern emitted from microwave antenna 74 of catheter 104 in a way that reduces heating in the direction of strip 102. Thus, incorporating strip 102 in catheter 104 has been shown to change the temperature distribution pattern of catheter 104, since the temperature of the tissue surrounding catheter 104 is directly related to the amount of energy delivered to the tissue. With strip 102 in place, catheter 104 has two treatment zones, a preferential heating zone and a non-preferential heating zone. The preferential heating zone experiences temperatures significantly higher than those experienced in the non-preferential heating zone. When catheter 104 is used for the treatment of BPH, the non-preferential heating zone corresponds to the rectal tissue region of the patient.

Figure 14:
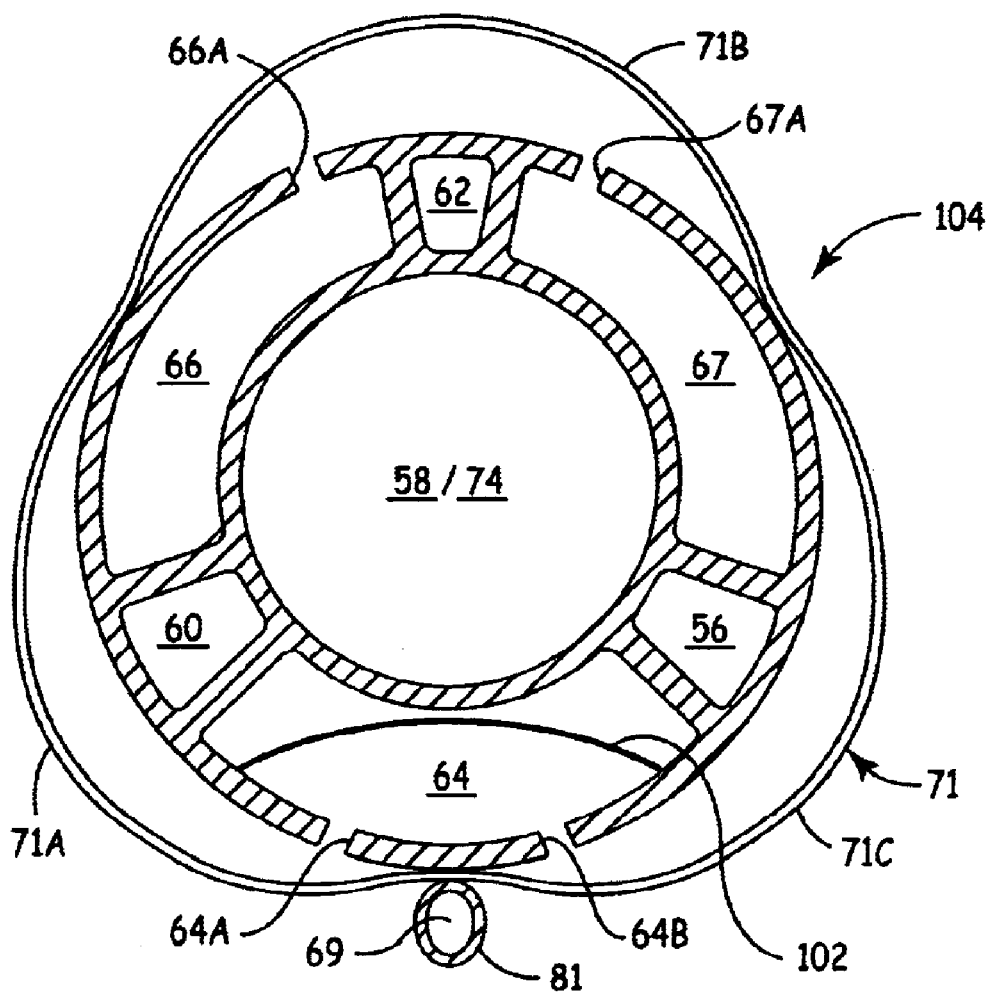
FIG. 14 is a cross-sectional view of the thermal therapy catheter of the present invention, taken along line 10—10 of FIG. 13.

FIG. 14 is a sectional view of catheter 104, taken along line 14–14 of FIG. 13. As shown in FIG. 14, metal strip 102 is positioned inside cooling lumen 64 of catheter 104 so that it is adjacent to microwave antenna 74. Metal strip 102 is approximately 2 inches long, 0.08 inches wide and 0.0053 inches in height. Metal strip 102 has a length slightly longer than microwave antenna 74 and a width slightly less than the radial width of cooling lumen 64. Strip 102 has a concave shape, which is formed by bending strip 102 over a mandrel after cutting strip 102 to size. The concave shape of metal strip 102 allows the strip 102 to be held in place within cooling lumen 64 by friction at three points of contact on the walls of cooling lumen 64. An end of metal strip 102 is secured to proximal end 54 of catheter 104 with an adhesive to prevent metal strip 102 from moving within cooling lumen 64. The concave shape of metal strip 102 also permits the cooling fluid to pass through cooling lumen 64 without interference from strip 102. Also, metal strip 102 does not interfere with fluid flow through the cooling lumen ports 64A and 64B.

To test the temperature distribution pattern generated by catheter 104, the catheter is placed in testing system 98 as shown in FIG. 8. The same parameters and testing procedure as described previously for catheter 28 is used to test catheter 104, with the individual testing phases performed at 5 and 10 minutes into the testing procedure.

Figure 15:
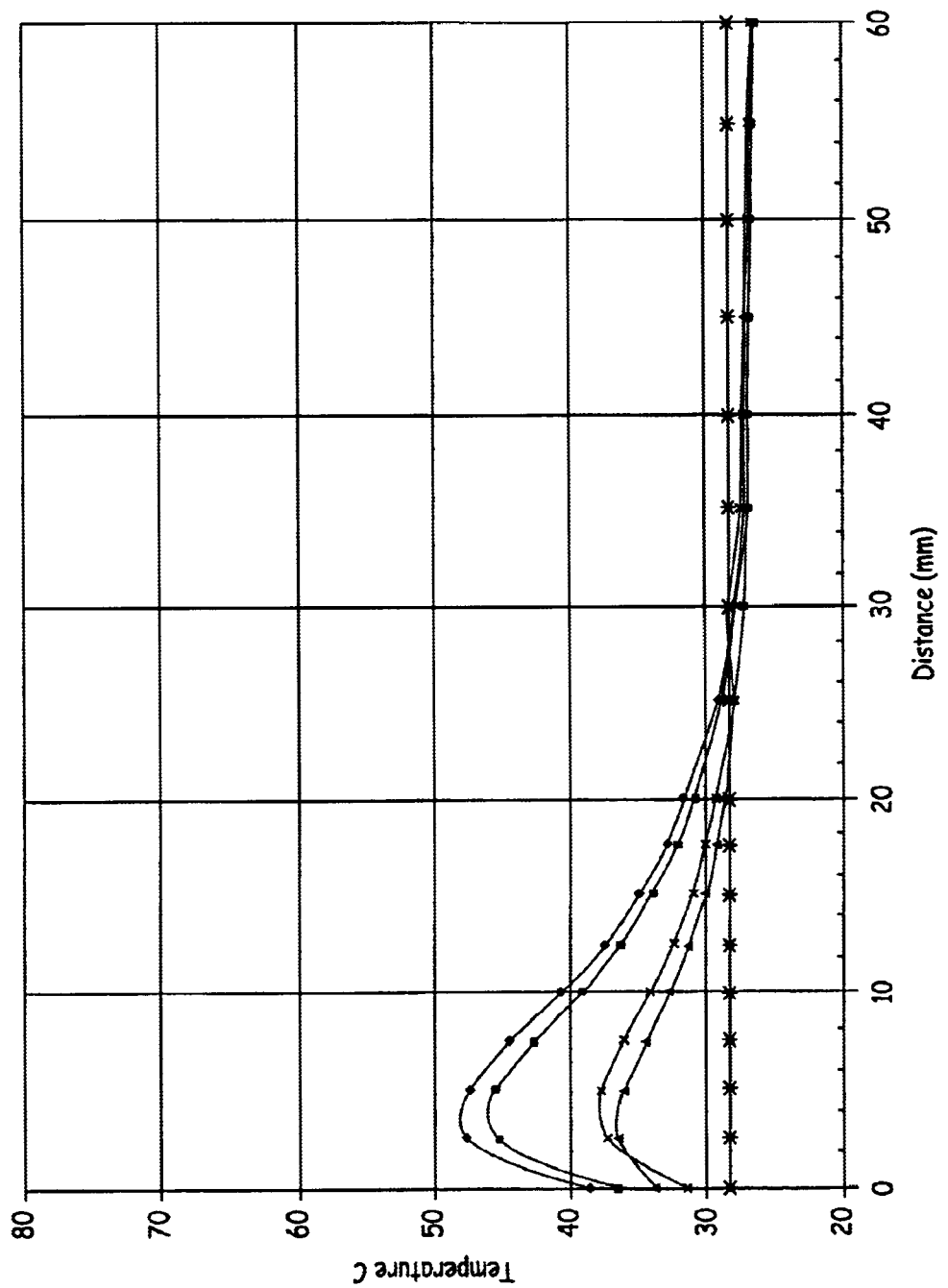
FIG. 15 is a graph showing the temperature of phantom tissue due to operation of the thermal therapy catheter of FIGS. 13–14 as a function of radial distance from the catheter, taken at 5 minutes into a testing procedure using the testing system of FIG. 8.
Figure 16:
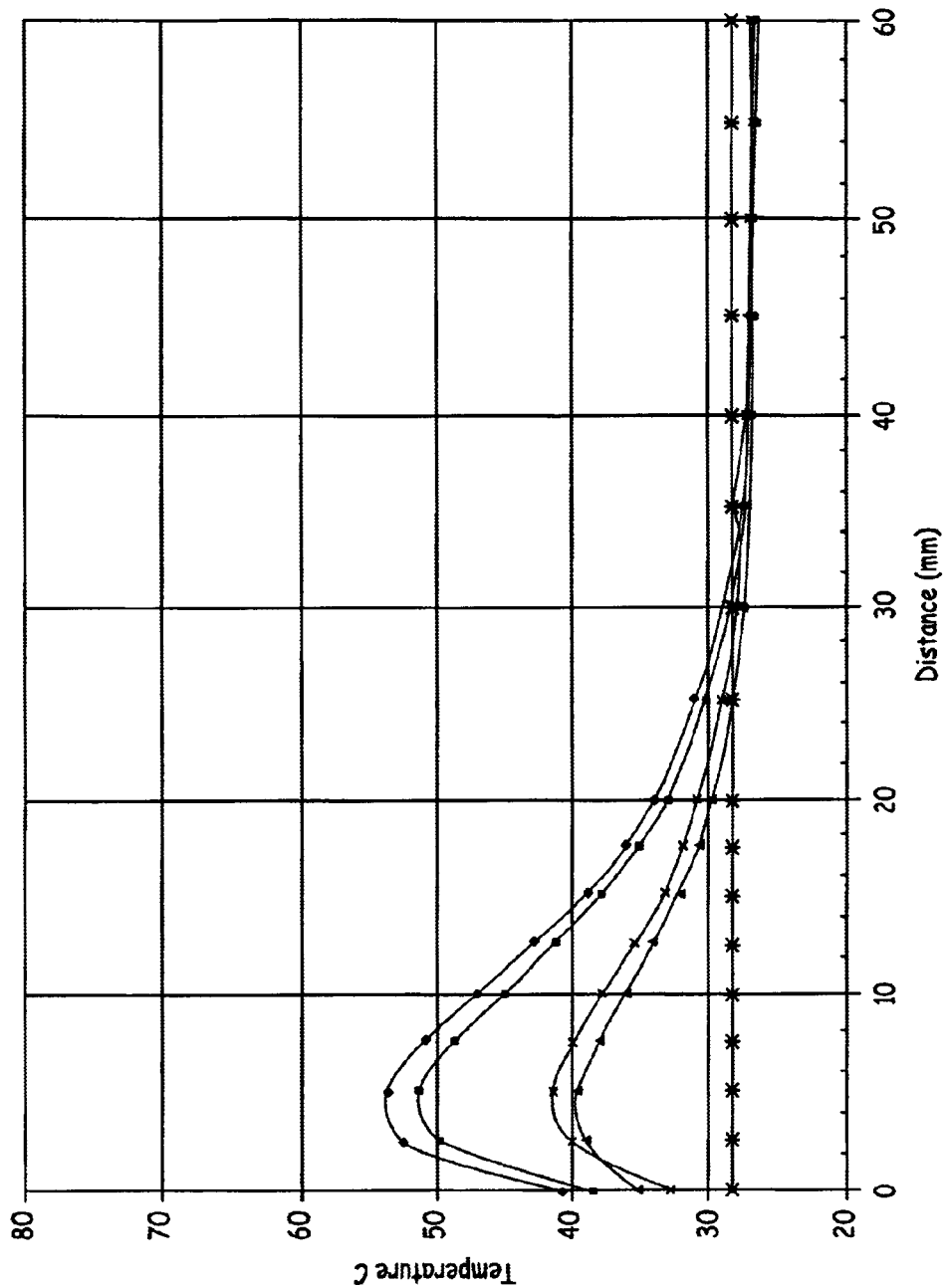
FIG. 16 is a graph showing the temperature of phantom tissue due to operation of the thermal therapy catheter of FIGS. 13–14 as a function of radial distance from the catheter, taken at 10 minutes into a testing procedure using the testing system of FIG. 8.

FIGS. 15–16 show temperature recordings of temperature sensors R1–R4 in comparison to the distances of temperature sensors R1–R4 from catheter 104 during a complete testing procedure. FIGS. 15–16 each represent temperature and distance data from a single testing phase. The vertical axes of FIGS. 15–16 correspond to the temperature of tissue medium 100, while the horizontal axes correspond to the radial distance away from catheter 104 of temperature sensors R1–R4. In FIGS. 15–16, temperature recordings of R1 are shown by diamond marks, temperature recordings of R2 are shown by square marks, temperature recordings of R3 are shown by triangle marks, and temperature recordings of R4 are shown by "x" marks. FIGS. 15–16 show that temperature sensors R1 and R2 record substantially dissimilar temperatures from the temperatures recorded by temperature sensors R3 and R4 at similar locations in tissue medium 100 throughout each testing phase. Thus, FIGS. 15–16 illustrate that catheter 104 produces a radially asymmetrical temperature distribution throughout tissue medium 100, and specifically, that catheter 104 generates two distinct heating zones in the tissue medium—a preferential heating zone and a non-preferential heating zone. The generation of two distinct heating zones is caused by metal strip 102, which attenuates microwave energy in the direction of the non-preferential heating zone. FIGS. 15–16 also illustrate that the temperature distribution throughout the preferential heating zone is generally uniform, and that the temperature distribution throughout the non-preferential heating zone is also generally uniform. Over the course of the complete testing procedure, FIGS. 15–16 indicate that the temperature of tissue medium 100 is steadily increased, and that temperature sensors R1–R4 record similarly shaped temperature-distance patterns during each testing phase.

FIG. 15 shows the temperature recordings of temperature sensors R1–R4 during a testing phase performed at 5 minutes into a testing procedure. Similar to FIG. 27, FIG. 28 shows that temperature sensors R1 and R2 record significantly higher temperatures than temperature sensors R3 and R4 in regions of tissue medium 100 which experience a substantial thermal change due to the energy generated by microwave catheter 104. The higher temperatures recorded by R1 and R2 are due to the fact that R1 and R2 are located in the preferential heating zone of catheter 104, while R3 and R4 are located in the non-preferential heating zone of catheter 104. The temperature variation between R1,R2 and R3,R4 decreases as temperature sensors R1–R4 increase in radial distance from catheter 104 and the heating effects of microwave antenna 74 therefore diminish in tissue medium 100. FIG. 15 also illustrates that temperature sensors R1 and R2 experience similar temperatures at similar radial distances, and temperature sensors R3 and R4 experience similar temperatures at similar radial distances. FIG. 15 indicates that temperatures throughout the preferential heating zone are generally uniform, and that temperatures throughout the non-preferential heating zone are generally uniform. Temperature sensors in the preferential heating zone, R1 and R2, experience temperatures approximately 10° higher than temperature sensors R3 and R4 in the non-preferential heating zone.

FIG. 16 shows the temperatures recorded by temperature sensors R1–R4 during a testing phase performed at 10 minutes into a testing procedure. FIG. 16 illustrates that temperature sensors R1 and R2 experience significantly higher temperatures than temperature sensors R3 and R4. Temperature sensors in the preferential heating zone, R1 and R2, once again experience temperatures about 10° 24 higher than temperature sensors R3 and R4 in the non-preferential heating zone, with peak temperatures being higher than the peak temperatures of the previous testing phase.

In FIGS. 15–16, the temperature variation between R1, R2 and R3, R4 is substantial for a distance from 0 to approximately 30 mm away from catheter 104. Beyond 30 mm from catheter 104, temperature sensors R1–R4 experience similar temperatures due to the decreased amount of energy delivered to the phantom tissue medium at those distances. FIGS. 15–16 illustrate that catheter 104 does not generate a radially symmetrical heating pattern in tissue medium 100, but instead, creates two distinct temperature zones—a preferential heating zone and a non-preferential heating zone, with the non-preferential heating zone being exposed to substantially lower amounts of thermal energy. The placement of metal strip 102 in catheter 104 creates the two distinct heating zones. Metal strip 102 attenuates microwave energy in the direction of the non-preferential heating zone, thereby decreasing the thermal energy delivered into the non-preferential heating zone during a treatment procedure. FIGS. 15–16 also illustrate that the temperature distribution throughout the preferential heating zone is generally uniform, and the temperature distribution throughout the non-preferential heating zone is also generally uniform.

Figure 17:
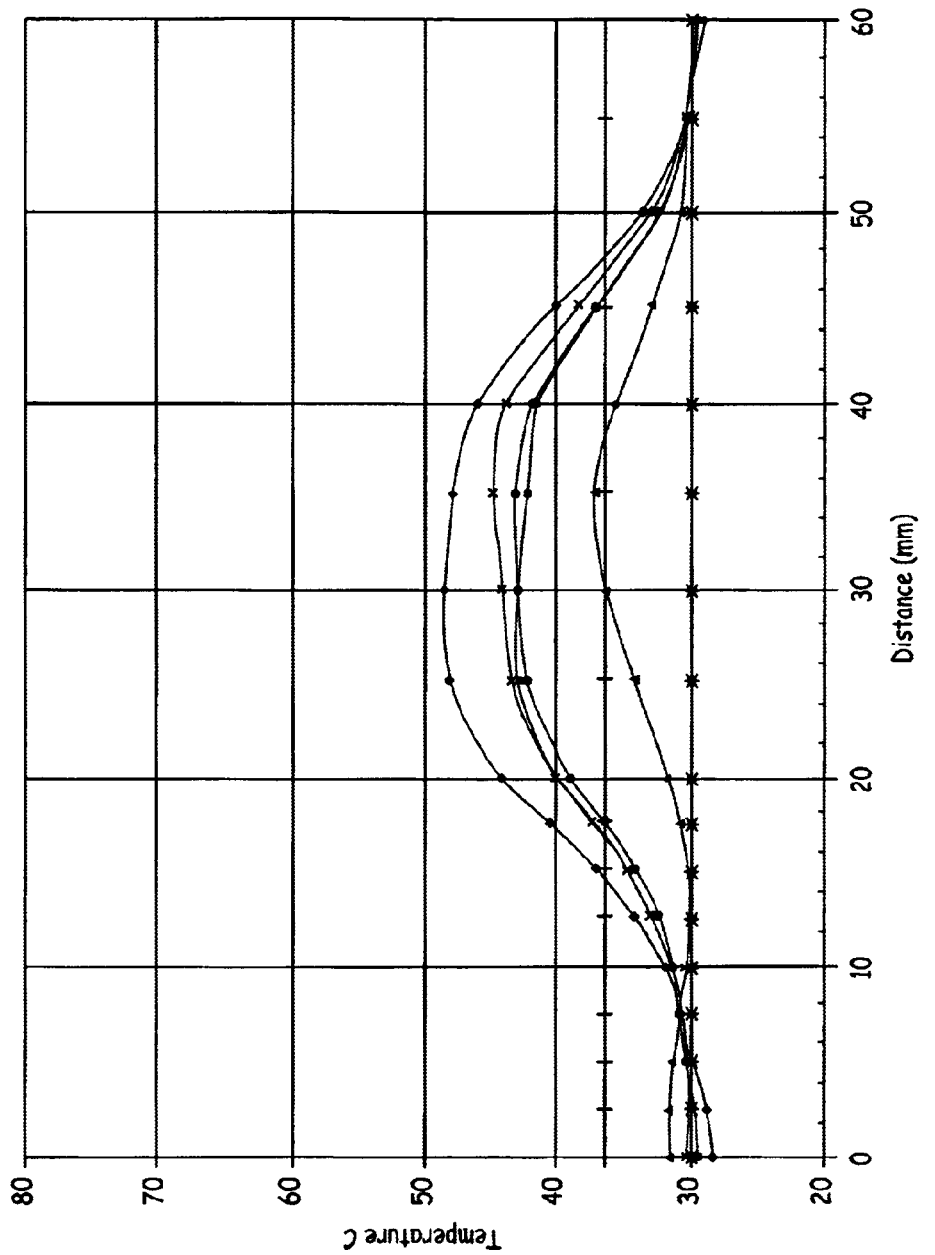
FIG. 17 is a graph showing an axial distribution of temperature in phantom tissue relative to the energy-emitting element of the thermal therapy catheter of FIGS. 13–14 during operation of the catheter, taken at 5 minutes into a testing procedure using the testing system of FIG. 8.
Figure 18:
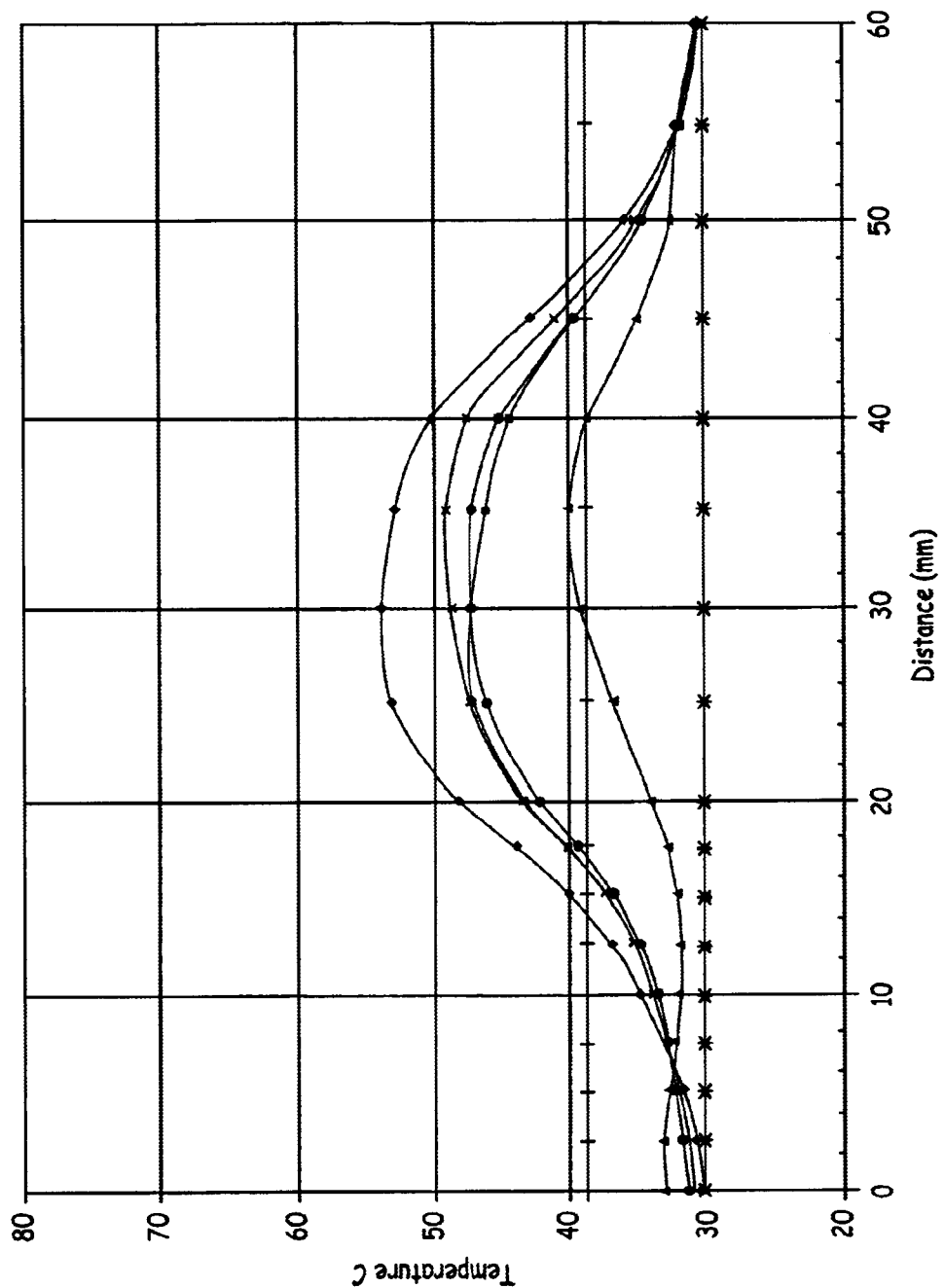
FIG. 18 is a graph showing an axial distribution of temperature in phantom tissue relative to the energy-emitting element of the thermal therapy catheter of FIGS. 13–14 during operation of the catheter, taken at 10 minutes into a testing procedure using the testing system of FIG. 8.

FIGS. 17–18 show temperature recordings of temperature sensors A1–A4 in comparison to the positions of temperature sensors A1–A4 along catheter 104 during a complete testing procedure. FIGS. 17–18 each represent temperature and distance data from a single testing phase. The vertical axes of FIGS. 17–18 correspond to the temperature of tissue medium 100, and the horizontal axes correspond to the axial position along catheter 104 of temperature sensors A1–A4. In FIGS. 17–18, temperature recordings of A1 are shown by diamond marks, temperature recordings of A2 are shown by square marks, temperature recordings of A3 are shown by triangle marks, and temperature recordings of A4 are shown by "x" marks. FIGS. 17–18 show that temperature sensor A1 records substantially higher temperatures and temperature sensor A3 records substantially lower temperatures than temperature sensors A2 and A4 at similar locations along catheter 104 in tissue medium 100 throughout each testing phase. Thus, FIGS. 17–18 illustrate that catheter 104 produces a radially asymmetrical temperature distribution along catheter 104. Over the course of the testing procedure, FIGS. 17–18 indicate that the temperature of tissue medium 100 is steadily increased, and that temperature sensors A1–A4 record similar temperature-distance patterns during each testing phase.

FIG. 17 illustrates the temperature recordings of temperature sensors A1–A4 during a testing phase performed at 5 minutes into a testing procedure. FIG. 17 shows that the temperatures recorded by temperature sensors A1–A4 gradually increase and then decrease over the course of a testing phase. This gradual increase and decrease in recorded temperatures corresponds to the movement of temperature sensors A1–A4 along the length of catheter 104. The temperature increase corresponds to temperature sensors A1–A4 sensing increased temperatures in tissue medium 100 as they move along the length of the energized microwave antenna 74 of catheter 104. The temperature decrease corresponds to the region of tissue medium 100 which is not adjacent to microwave antenna 74 and thus is not exposed to as much thermal energy as tissue directly adjacent to antenna 74. FIG. 17 illustrates that temperature sensor A1 experiences substantially higher temperatures and temperature sensor A3 experiences substantially lower temperatures than temperature sensors A2 and A4 as the temperature of tissue medium 100 increases. Temperature sensor A3 experiences lower temperatures because it is located in the non-preferential heating zone of catheter 104, due to microwave attenuation by metal strip 102. Conversely, temperature sensor A1 is located in the preferential heating zone of catheter 104, and thus, experiences higher temperatures. Temperature sensors A2 and A4 experience similar temperatures at similar axial distances, with the temperatures experienced being between the temperatures experienced by temperature sensors A1 and A3.

FIG. 18 corresponds to the temperature recordings of temperature sensors A1–A4 during a testing phase performed at 10 minutes into a testing procedure. FIG. 18, similar to FIG. 17, illustrates a temperature difference between temperature sensors A1 and A3 and temperature sensors A2 and A4. Temperature sensor A1 in the preferential heating zone experiences substantially higher temperatures than temperature sensor A3, which is located in the non-preferential heating zone. Temperature sensors A2 and A4 experience similar temperatures, with those temperatures being between the temperatures experienced by temperatures sensors A1 and A3. FIG. 18 also illustrates that the temperature distribution is axially uniform throughout the preferential heating zone, and also that the temperature distribution is axially uniform throughout the non-preferential heating zone. The peak temperatures experienced by temperature sensors A1–A4 in tissue medium 100 are greater than those shown in FIG. 17.

FIGS. 15–16 display the temperature data recorded by temperature sensors R1–R4 throughout a complete testing procedure. FIGS. 15–16 each show a similar pattern for temperature variation (a gradual increase and then decrease in temperatures of tissue medium 100) as temperature sensors R1–R4 move radially away from catheter 104. FIGS. 15–16 show that catheter 104 does not heat tissue medium 100 symmetrically in radial directions. Instead, two heating zones are generated by catheter 104—a preferential heating zone and a non-preferential heating zone. The preferential heating zone experiences substantially higher temperatures than the non-preferential heating zone. However, the temperature distributions within the preferential heating zone and the non-preferential heating zones are generally uniform.

FIGS. 17–18 display the temperature data recorded by temperature sensors A1–A4 throughout a complete testing procedure. Similar to temperature sensors R1–R4, temperature sensors A1–A4 show a radially asymmetrical heating distribution in tissue medium 100. Thus, FIGS. 17–18 in combination with FIGS. 15–16 con firm that catheter 104 generates two zones of thermal energy within tissue medium 100, and that one of the heating zones experiences substantially greater temperatures than the other zone. The generation of the two distinct heating zones is a result of metal strip 102 attenuating microwave energy in the direction of the non-preferential heating zone.

The present invention is a simple, inexpensive modification to a microwave thermal treatment catheter system that produces an asymmetrical heating pattern, thereby enabling a clinician to utilize the catheter in such a manner as to expose tissues in a first selected region to necrosing levels of energy at a large depth and to expose tissues in a second selected region to necrosing levels of energy at a smaller depth, to protect healthy tissues adjacent the second selected region from thermal damage. The invention is particularly useful for treatment of a prostate from a urethral catheter, employed to necrose prostate tissue in a region anterior to the urethra (opposite the rectum) to a first depth and to necrose prostate tissue in a region posterior to the urethra (adjacent the rectum) to a second depth, less than the first depth, without thermally damaging the rectum.

Although the present invention has been described with reference to preferred embodiments, workers skilled in the art will recognize that changes may be made in form and detail without departing from the spirit and scope of the invention.

What is claimed is:

1. A device for preferentially treating tissue adjacent to a body lumen, the device comprising:

a catheter shaft having an outer surface, the catheter shaft being insertable into the body lumen;

an energy-emitting element carried by the catheter shaft, the energy-emitting element being operable to radiate a generally symmetrical energy pattern;

a plurality of cooling lumens in the catheter shaft around the energy-emitting element, the plurality of cooling lumens being configured for circulation of a fluid therethrough;

means located in at least one of the plurality of cooling lumens for attenuating energy radiated by the energy-emitting element.

2. The device of claim 1, wherein the means for attenuating energy comprises a metal strip in at least one of the plurality of cooling lumens.

3. The device of claim 1, wherein the means for attenuating energy is located to produce an asymmetrical energy pattern in the tissue adjacent to the body lumen upon operation of the energy-emitting element.

4. The device of claim 1, further comprising:

a multi-lobe balloon around the outer surface of the catheter shaft adjacent the energy-emitting element, opposing ends of the multi-lobe balloon being sealingly connected to the catheter shaft to form a chamber between the multi-lobe balloon and the outer surface of the catheter shaft; and means for circulating a fluid through the plurality of cooling lumens and between the outer surface of the catheter shaft and the multi-lobe balloon in a defined fluid flow path.

5. The device of claim 4, wherein the plurality of cooling lumens comprises:

at least one fluid intake lumen in the catheter shaft, the at least one fluid intake lumen being in fluid communication with at least one lobe of the multi-lobe balloon; and at least one fluid exhaust lumen in the catheter shaft, the at least one fluid exhaust lumen being in fluid communication with at least one lobe of the multi-lobe balloon.

6. The device of claim 5, further comprising a cooling system providing fluid to the at least one fluid intake lumen and receiving fluid from the at least one fluid exhaust lumen.

7. The device of claim 4, further comprising:

a temperature sensor fiber lumen in the catheter shaft;

a temperature sensor fiber tube attached to the outer surface of the catheter shaft between lobes of the multi-lobe balloon;

a channel in the catheter shaft connecting the temperature sensor fiber lumen and the temperature sensor fiber tube; and a temperature sensor fiber extending through the temperature sensor fiber lumen, the channel and the temperature sensor fiber tube to sense a temperature of tissue immediately adjacent to the temperature sensor fiber tube.

8. The device of claim 4, further comprising:
a urine drainage lumen in the catheter shaft.

9. The device of claim 4, further comprising:
a balloon inflation lumen in the catheter shaft; and
a retention balloon at an end of the catheter shaft, the retention balloon being in fluid communication with the balloon inflation lumen so as to be inflatable in a bladder to secure the catheter shaft in place in the urethra.

10. A device for preferentially treating tissue adjacent to a body lumen, the device comprising:
a catheter shaft having an outer surface, the catheter shaft being insertable into the body lumen;
an energy-emitting element carried by the catheter shaft, the energy-emitting element being operable to radiate a generally symmetrical energy pattern;
a plurality of cooling lumens in the catheter shaft around the energy-emitting element, the plurality of cooling lumens being configured for circulation of a fluid therethrough; and
an attenuating element in at least one of the plurality of cooling lumens, the attenuating element being arranged to modify the generally symmetrical energy pattern radiated by the energy-emitting element to deliver an asymmetrical energy pattern to the tissue adjacent to the body lumen.

11. The device of claim 10, wherein the attenuating element comprises a metal strip in at least one of the plurality of cooling lumens.

12. The device of claim 10, wherein the attenuating element is arranged to produce a first energy pattern region and a second energy pattern region upon operation of the energy-emitting element, the energy delivered in the first energy pattern region being greater than the energy delivered in the second energy pattern region.

13. The device of claim 12, wherein the catheter shaft is insertable into a urethra and the attenuating element is arranged to produce the first energy pattern region in prostate tissue distant from a rectum and to produce the second energy pattern region in prostate tissue adjacent to the rectum upon operation of the energy-emitting element.

14. The device of claim 10, further comprising:
a multi-lobe balloon around the outer surface of the catheter shaft adjacent the energy-emitting element, opposing ends of the multi-lobe balloon being sealingly connected to the catheter shaft to form a chamber between the multi-lobe balloon and the outer surface of the catheter shaft; and
means for circulating a fluid through the plurality of cooling lumens and between the outer surface of the catheter shaft and the multi-lobe balloon in a defined fluid flow path.

15. The device of claim 14, wherein the plurality of cooling lumens comprises:
at least one fluid intake lumen in the catheter shaft, the at least one fluid intake lumen being in fluid communication with at least one lobe of the multi-lobe balloon; and
at least one fluid exhaust lumen in the catheter shaft, the at least one fluid exhaust lumen being in fluid communication with at least one lobe of the multi-lobe balloon.

16. The device of claim 15, further comprising a cooling system providing fluid to the at least one fluid intake lumen and receiving fluid from the at least one fluid exhaust lumen.

17. The device of claim 14, further comprising:
a temperature sensor fiber lumen in the catheter shaft;
a temperature sensor fiber tube attached to the outer surface of the catheter shaft between lobes of the multi-lobe balloon;
a channel in the catheter shaft connecting the temperature sensor fiber lumen and the temperature sensor fiber tube; and
a temperature sensor fiber extending through the temperature sensor fiber lumen, the channel and the temperature sensor fiber tube to sense a temperature of tissue immediately adjacent to the temperature sensor fiber tube.

18. The device of claim 14, further comprising:
a urine drainage lumen in the catheter shaft.

19. The device of claim 14, further comprising:
a balloon inflation lumen in the catheter shaft; and
a retention balloon at an end of the catheter shaft, the retention balloon being in fluid communication with the balloon inflation lumen so as to be inflatable in a bladder to secure the catheter shaft in place in the urethra.

20. A method of preferentially treating tissue adjacent to a body lumen, the method comprising:
inserting a catheter shaft into the body lumen, the catheter shaft including an energy-emitting element radiating energy in a generally symmetrical energy pattern and a plurality of cooling lumens around the energy-emitting element;
circulating a fluid in the cooling lumens; and
attenuating at least a portion of the energy radiated from the energy-emitting element to produce an asymmetrical energy pattern in the tissue adjacent to the body lumen.

21. The method of claim 20, wherein the metal strip is arranged to produce a first energy pattern region and a second energy pattern region upon operation of the energy-emitting element, the energy delivered in the first energy pattern region being greater than the energy delivered in the second energy pattern region.

22. The method of claim 21, wherein the catheter shaft is inserted into a urethra and the metal strip is arranged so as to produce the first energy pattern region in prostate tissue distant from a rectum and to produce the second energy pattern region in prostate tissue adjacent to the rectum upon operation of the energy-emitting element.

* * * * *

UNITED STATES PATENT AND TRADEMARK OFFICE
CERTIFICATE OF CORRECTION

PATENT NO. : 6,740,108 B1
DATED : May 25, 2004
INVENTOR(S) : Dale Just et al.

It is certified that error appears in the above-identified patent and that said Letters Patent is hereby corrected as shown below:

Column 15,
Line 45, delete "con firm", insert -- confirm --

Column 18,
Line 41, delete "attenuating", insert -- inserting a metal strip into at least one of the plurality of cooling lumens to attenuate --

Signed and Sealed this

Twenty-third Day of November, 2004

JON W. DUDAS
*Director of the United States Patent and Trademark Office*